US 9,234,852 B2

(12) United States Patent
Gladnick et al.

(10) Patent No.: US 9,234,852 B2
(45) Date of Patent: Jan. 12, 2016

(54) SYSTEMS AND METHODS FOR CONTROLLING STROBE ILLUMINATION

(75) Inventors: Paul G. Gladnick, Seattle, WA (US); Mark Delaney, Shoreline, WA (US)

(73) Assignee: MITUTOYO CORPORATION, Kanegawa (JP)

( * ) Notice: Subject to any disclaimer, the term of this patent is extended or adjusted under 35 U.S.C. 154(b) by 1088 days.

(21) Appl. No.: 13/137,514

(22) Filed: Aug. 23, 2011

(65) Prior Publication Data
US 2011/0310270 A1 Dec. 22, 2011

Related U.S. Application Data

(63) Continuation-in-part of application No. 11/191,969, filed on Jul. 29, 2005, now Pat. No. 8,045,002.

(51) Int. Cl.
*G01N 21/88* (2006.01)
*H04N 5/235* (2006.01)

(52) U.S. Cl.
CPC .......... *G01N 21/8806* (2013.01); *H04N 5/2354* (2013.01); *G01N 2021/8838* (2013.01)

(58) Field of Classification Search
CPC ................................................ G01N 21/8806
See application file for complete search history.

(56) References Cited

U.S. PATENT DOCUMENTS

| | | | |
|---|---|---|---|
| 4,305,658 A | 12/1981 | Yoshida | |
| 5,548,418 A | 8/1996 | Gaynor et al. | |
| 6,038,067 A | 3/2000 | George | |
| 6,239,554 B1 | 5/2001 | Tessadro et al. | |
| 6,324,298 B1 | 11/2001 | O'Dell et al. | |
| 6,542,180 B1 | 4/2003 | Wasserman et al. | |
| 6,545,758 B1 | 4/2003 | Sandstrom | |
| 6,627,863 B2 | 9/2003 | Wasserman | |
| 6,690,474 B1 | 2/2004 | Shirley | |
| 6,738,131 B2 | 5/2004 | Tanabata et al. | |
| 6,741,768 B2 | 5/2004 | Culver et al. | |
| 6,937,321 B2 | 8/2005 | Tanabata et al. | |
| 7,030,351 B2 | 4/2006 | Wasserman et al. | |
| 7,127,159 B2 | 10/2006 | Gladnick et al. | |
| 2002/0067477 A1 | 6/2002 | Morita et al. | |
| 2002/0067880 A1 | 6/2002 | Huber et al. | |
| 2004/0075882 A1 | 4/2004 | Meisburger | |

(Continued)

FOREIGN PATENT DOCUMENTS

| EP | 0 572 336 A1 | 12/1993 |
|---|---|---|
| EP | 1 533 996 A1 | 5/2005 |

(Continued)

*Primary Examiner* — Sath V Perungavoor
*Assistant Examiner* — James Pontius
(74) *Attorney, Agent, or Firm* — Oliff PLC

(57) ABSTRACT

The repeatability of strobe illumination for image exposure is improved over a wide dynamic range in a machine vision system wherein a relationship between a camera integration period and a pulse duration of a strobe light generator control the effective exposure of a camera image during a timing overlap between a beginning of the camera integration period and an end of the pulse duration. To avoid noise in the illumination, the illumination pulse duration may start, the camera integration period may begin after a delay relative to that start and not later than the end of the pulse duration, the pulse duration may end, and the camera integration period may end not earlier than the end of the pulse duration. The timing overlap may also be synchronized with a periodic ripple component in the strobe illumination, to provide improved repeatability.

19 Claims, 17 Drawing Sheets

(56) References Cited

U.S. PATENT DOCUMENTS

| | | |
|---|---|---|
| 2004/0156054 A1 | 8/2004 | Christoph |
| 2004/0223053 A1 | 11/2004 | Gladnick et al. |
| 2006/0018025 A1 | 1/2006 | Sharon et al. |
| 2006/0024040 A1* | 2/2006 | Gladnick et al. .............. 396/182 |
| 2007/0159600 A1 | 7/2007 | Gil et al. |
| 2010/0245566 A1 | 9/2010 | Lev et al. |

FOREIGN PATENT DOCUMENTS

| | | |
|---|---|---|
| EP | 1286 134 B1 | 5/2006 |
| EP | 1 533 996 B1 | 12/2006 |
| EP | 1 748 643 B1 | 9/2009 |
| JP | A-05-508702 | 12/1993 |
| JP | A-2002-975815 | 3/2002 |
| JP | A-2002-168800 | 6/2002 |
| JP | A-2003-004441 | 1/2003 |
| JP | A-2005-156554 | 6/2005 |
| WO | WO 91/12489 | 8/1991 |
| WO | WO 01/49043 A1 | 7/2001 |
| WO | WO 03/009070 A2 | 1/2003 |
| WO | WO 2004/091362 A1 | 10/2004 |

\* cited by examiner

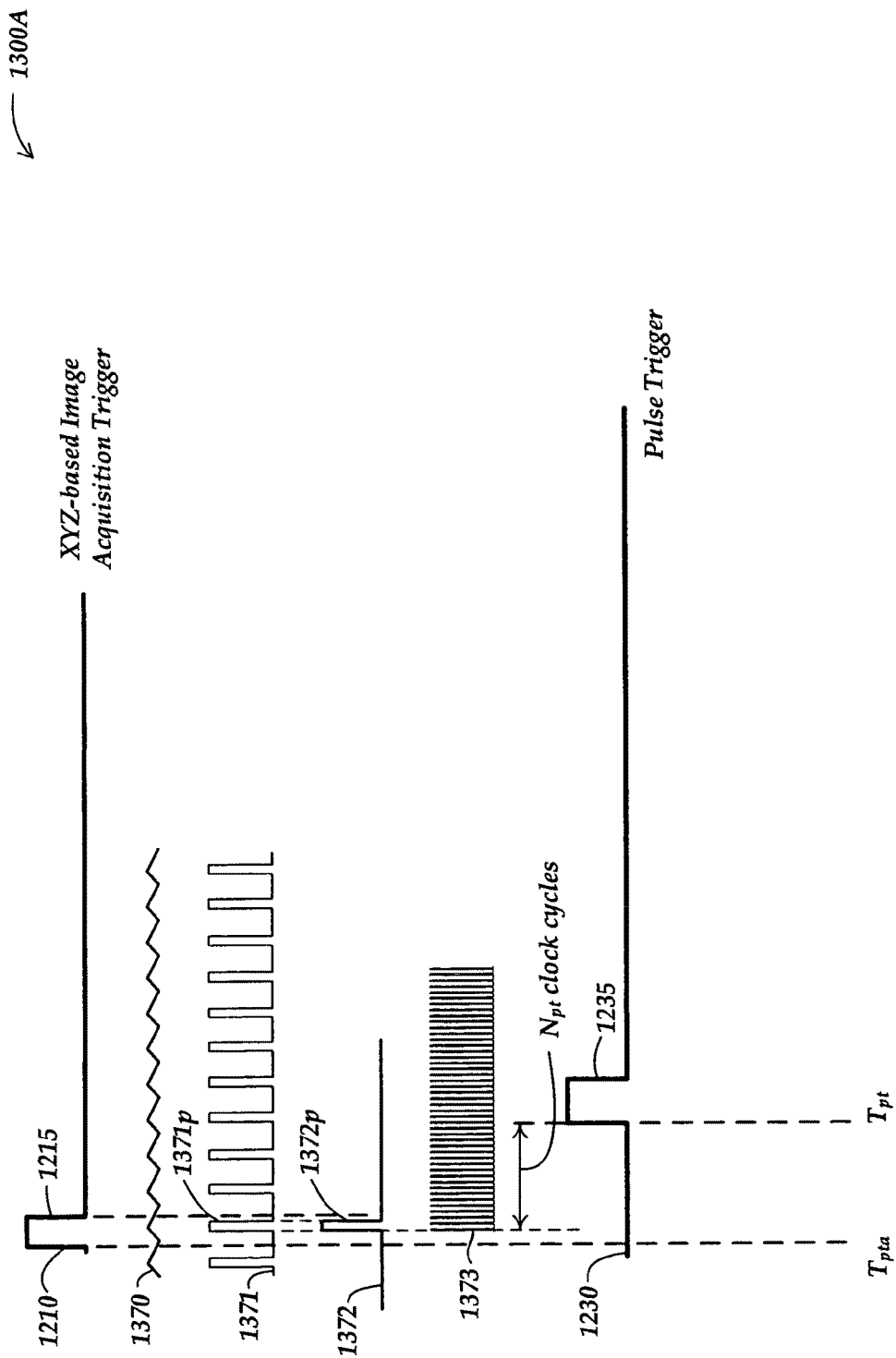

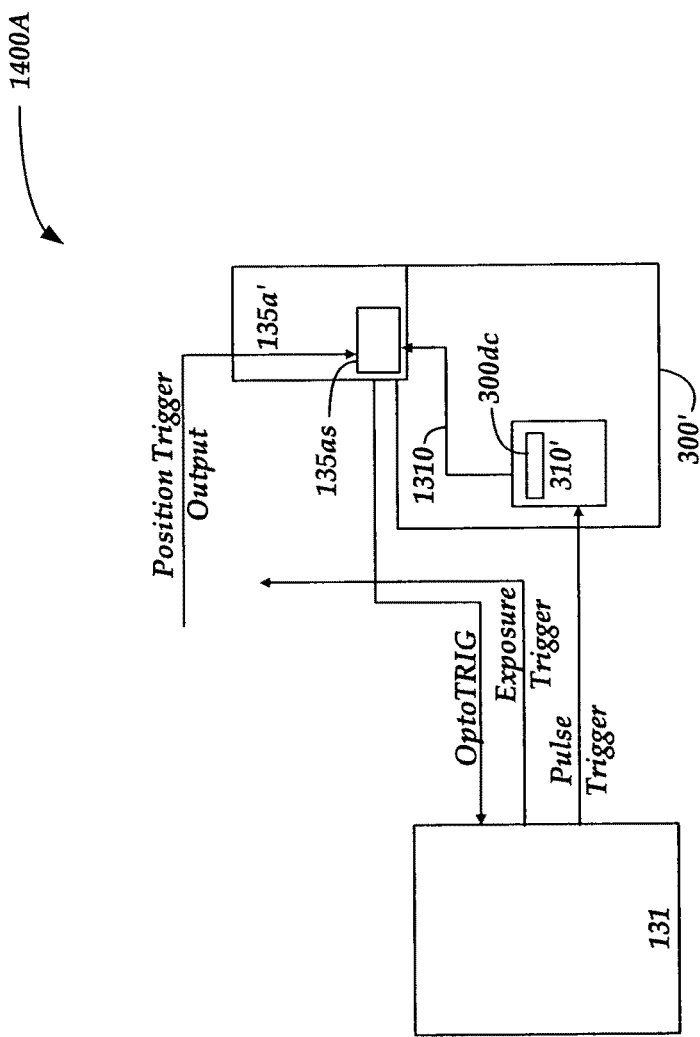

SYSTEMS AND METHODS FOR CONTROLLING STROBE ILLUMINATION

CROSS-REFERENCE(S) TO RELATED APPLICATION(S)

This application is a continuation-in-part of U.S. patent application Ser. No. 11/191,969, filed Jul. 29, 2005, priority from the filing date of which is hereby claimed under 35 U.S.C. §120.

BACKGROUND

This invention relates to systems and methods that select light source channels and control light intensity and direction for precision machine vision inspection using a transient light source.

Methods for operating a machine vision inspection system with a camera and a stage that are movable relative to one another to focus on and inspect selected features of a workpiece on the stage are generally known. Precision machine vision inspection systems may be used to obtain precise dimensional measurements of inspected objects and to inspect various other object characteristics.

Such systems may include a computer, a camera and/or optical system and a precision stage that may be movable in multiple directions to allow the camera to scan the features of a workpiece that is being inspected. One exemplary prior art system, of a type that may be characterized as a general-purpose "off-line" precision vision system, is the commercially available Quick Vision™ series of vision inspection machines and QVPak® software available from Mitutoyo America Corporation (MAC), located in Aurora, Ill.

Such general-purpose "off-line" precision vision systems often include a programmable illumination system and a lens turret with lenses of various magnifications, for example, to increase versatility of the image systems and provide the ability to rapidly change configuration and imaging parameters for the vision systems to perform a wide variety of inspection tasks. There is a common need to inspect various types of objects or inspection workpieces, or various aspects of a single workpiece, using various combinations of magnifications and the programmable illumination settings.

General purpose precision machine vision inspection systems, such as the Quick Vision™ system, are also generally programmable and operable to provide automated video inspection. Such systems may include features and tools that simplify the programming and operation of such systems, such that operation and programming may be performed reliably by "non-expert" operators. For example, U.S. Pat. No. 6,542,180, which is incorporated herein by reference in its entirety, teaches a vision system that uses automated video inspection. The system performs operations to adjust the lighting used to illuminate a workpiece feature based on a plurality of selected regions of a feature image.

Imaging systems are widely used to inspect workpieces being transported through a manufacturing process. Equipment such as machine vision inspection systems often capture images of the workpieces using a camera, for example, and process captured images to verify various workpiece dimensions by identifying edges of relevant features in the images.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The precise location and repeatability of where an edge is detected within an image depends on the lighting of the workpiece during image capture. Edge artifacts or edge-shifting may be created by lighting-specific shadows cast due to sub-optimal direction of the illumination of the workpiece. Over- or under-exposure may reduce the ability to accurately detect an edge, and decrease measurement repeatability. To increase productivity, workpieces may be kept in motion, even during image capture. This places an additional burden on illumination systems to minimize blurring caused by the motion. Such factors frequently limit the accuracy with which the edge of a feature may be located within an image and/or the velocity that may be tolerated during image capture. Thus, improvements in workpiece illumination control technology would be very desirable.

Various exemplary embodiments provide systems and methods for strobe illumination for imaging a workpiece. For example, the systems and methods may be used for controlling image exposure strobe illumination in a machine vision system which is configured for illuminating a workpiece such that it may be imaged by a camera of the machine vision system while moving at high speed. Exemplary systems may include an illumination source (e.g. a strobe light generator), an image acquisition device (e.g. the machine vision system camera) and a control system (e.g. a control system portion of the machine vision system). The illumination source may emit light of one or more visible or invisible wavelengths of radiation that are suitable for imaging the workpiece, as a transient flash or pulse to the workpiece. The transient flash or pulse, also referred to as an illumination pulse, may occur in response to a lamp trigger, also referred to as a pulse trigger. In some embodiments, the illumination source may emit the light at an illumination intensity that rises from a begin threshold to a peak and afterwards diminishes to an end threshold during a flash duration. The image acquisition device may capture the light associated with the workpiece for an exposure duration, also referred to as camera integration period, started in response to an exposure trigger, also referred to as a camera integration trigger. The control system may control the illumination source and the image acquisition device to provide a desired overlap between the exposure duration or camera integration period and the flash duration. In one embodiment, the beginning of the exposure duration may precede the lamp trigger by a lamp lag period. The lamp trigger may be set to synchronize or adjust a timing relationship between an end of the exposure duration and the illumination intensity profile of the flash, in order to control the effective exposure time of an image.

Embodiments wherein the beginning of the exposure duration or camera integration period precedes the illumination pulse and then ends during the illumination pulse, as outlined above, allow for effective image exposure times (that is, lengths of time) which are less than both the illumination pulse duration and the camera integration period, and are suitable for some strobe illumination systems and applications. Short effective image exposure times provided by this "overlap" control technique allow a clear "frozen" image of a workpiece at increased motion speeds, which increases inspection throughput. However, for systems and/or applications in which the shortest possible effective image exposure times are desired, an embodiment wherein the illumination pulse duration is triggered to start first, the camera integration period is triggered to start after a delay relative to the start of the illumination pulse duration, and the illumination pulse duration ends during the camera integration period, may be more advantageous for avoiding illumination noise, as outlined below, while also providing shorter effective image exposure times.

For example, increasingly powerful LED strobe sources allow and/or require shorter image exposure times, but such strobe sources may include illumination noise components as described in greater detail below. It should be appreciated that decreasing exposure times means that any noise component (e.g. intensity variations) in the illumination pulse is averaged into a shorter image exposure time. As a result, image exposure repeatability suffers, particularly for shorter exposure times. Reduced image exposure repeatability degrades potential accuracy in certain operations (e.g. autofocus and/or focus height determination, as one example), introducing errors that are significant, particularly in precision machine vision inspection systems. Thus, it is important to further decrease and/or compensate illumination noise components that may otherwise be included in short image exposure times.

Powerful LED strobe sources may be driven using currents as large as 40 amperes (40 A), or more. An initial noise period of intensity noise of the illumination pulse may be associated with the transient circuit effects of starting such a high current pulse into the LED. Thus, in some embodiments, the control system portion is configured to control a timing relationship between the camera integration period and a pulse duration of the radiation emitted by the strobe light generator to control an image exposure of a camera image during a timing overlap which occurs between a beginning of the camera integration period and an end of the pulse duration. The timing relationship may be controlled such that the illumination pulse duration starts, the camera integration period begins after a delay relative to a start of the pulse duration and not later than the end of the pulse duration, the pulse duration ends, and the camera integration period ends not earlier than the end of the pulse duration. In various embodiments, the camera integration period ends after the end of the pulse duration. By providing the image exposure during the timing overlap at the end of the pulse duration, the aforementioned initial noise period of the illumination pulse duration is avoided, in order to provide more repeatable image illumination levels (e.g. for repeated images, such as an image stack that is acquired and used in various known autofocus operations). Thus, this method provides the ability to increase the dynamic range of exposures for which simple time-based control may be used, without degrading repeatability of the exposure level, even for very short pulse durations. In various embodiments, the control system portion is configured to variably control a length of the timing overlap in order to variably control the image exposure of a camera image. In some embodiments the pulse duration is set at a constant value (e.g at a value in a range of 5-150 µs, for example) and the delay is controlled in order to control the length of the timing overlap. In some embodiments the delay is set to a constant value (e.g. at a value of 25 µs, for example) and the delay pulse duration is controlled in order to control the length of the timing overlap. In some embodiments, the machine vision system comprises an image brightness control and the control system portion is configured to control the length of the timing overlap based on a setting of the image brightness control. The image brightness control may comprise a lowest setting which corresponds to a state wherein the length of the timing overlap is approximately zero.

Another potential source on non-repeatable illumination levels from powerful LED strobe sources may arise from a periodic ripple component in the illumination intensity due to a corresponding ripple in the high-current drive circuit. It is difficult to economically eliminate such ripple components (e.g. on the order of 1-2% of the drive level) in high current drive circuits that must provide fast on/off switching times for strobe control. If different image exposures have the same effective duration (e.g. the same "overlap" timing outlined above), but are timed differently relative to the phase of the periodic ripple, then both the instantaneous and average illumination intensity will vary despite the otherwise consistent timing. This may affect the accuracy and/or repeatability of images used for edge detection, autofocus, and the like, at a level that is significant for precision machine vision inspection systems. Therefore, in various embodiments, the control system portion is configured to synchronize the signals that control the image exposure timing with the periodic ripple component. In various embodiments, a signal derived from the timing of the ripple in the drive circuit is used to start counting of a high-speed clock which governs the timing overlap that determines the image exposure, such that the image exposure is synchronized with the ripple component in the illumination intensity. In some embodiments, the strobe light generator comprises an illumination source and a drive circuit that provides a drive signal that provides power to the illumination source, the drive signal exhibits a periodic ripple component, and the control system portion is configured to synchronize the timing overlap with the periodic ripple component. In some embodiments, the end of the timing overlap is synchronized with the periodic ripple component. In some such embodiments, the start of the pulse duration may be consistently synchronized relative to the periodic ripple component, the pulse duration may have a constant value, and delay may be controlled in order to control a length of the timing overlap. In other embodiments, the start of the timing overlap is synchronized with the periodic ripple component. In some such embodiments, the control system portion comprises a clock portion, and the control system portion is configured to consistently synchronize the beginning of the camera integration period relative to the periodic ripple component and end the pulse duration based on a number of clock cycles relative to the beginning of the camera integration period, in order to control a length of the timing overlap.

The aforementioned systems and methods for strobe illumination and image exposure control may be used independently or combined, and may be combined with various other features disclosed herein. For example, in various exemplary embodiments, exposure triggers may correspond to predetermined positions of the workpiece relative to a coordinate space used by the machine vision inspection system. Furthermore, in various exemplary embodiments, such systems and methods may further include a controllable spatial light modulator (SLM) configured to provide a light channel aperture positioned to controllably attenuate the radiation emitted by the strobe light generator, wherein the control system portion is configured to control the image exposure of the camera image based on controlling the timing overlap, in combination with controlling the light channel aperture to attenuate the radiation emitted by the strobe light generator, in order to further control the image exposure. In some embodiments, the SLM comprises an array of attenuating elements that are arranged and controlled to distribute the light from one or more illumination sources controlled as outlined above. The array may include elements that selectively either block, partially transmit, or transmit the light toward respective lighting channels, such as respective optical fiber bundles. Each respective lighting channel may direct the light along a path to project commanded illumination from a respective position and/or angle of incidence relative to the workpiece. In addition, the aforementioned techniques can be used in conjunction with adjustments to a drive current level and/or drive current modulation, or the like, in order to further extend the controllable range of illumination.

BRIEF DESCRIPTION OF THE DRAWINGS

Various details are described below with reference to the following figures, wherein:

FIGS. 13A and 13B show timing diagrams illustrative of first and second techniques, respectively, usable for synchronizing an image exposure with a periodic ripple component in illumination intensity in a third embodiment of exemplary camera and flash triggers associated with strobe illumination and exposure control;

FIGS. 14A and 14B show block diagrams of exemplary controller circuits and signals associated with a light generator and a vision measuring machine, usable to generate the signals shown in FIGS. 13A and 13B, respectively.

DETAILED DESCRIPTION OF EMBODIMENTS

The following detailed description refers to multi-channel strobe illumination for magnified image acquisition. The strobe illumination source may refer to a Xenon flashlamp, for example. Alternatively, the strobe illumination source may refer to a high power LED source. However, the principles described herein may be equally applied to any known or later-developed transient illumination sources, beyond the examples specifically discussed herein.

Exemplary systems and methods for machine vision inspection, as provided herein, may be used in conjunction with systems and methods disclosed in U.S. Pat. No. 7,030,351, issued Apr. 18, 2006, directed to automatic focusing, and/or U.S. Pat. No. 7,127,159, issued Oct. 24, 2006, directed to strobe illumination, and/or U.S. Patent Application Publication No. US 2004-0223053 A1, published Nov. 11, 2004 (now abandoned), directed to improved machine vision inspection throughput, each of which is incorporated herein by reference in its entirety.

Various methods and GUIs usable for determining an optimum light setting to be used with rapid auto focus systems that determine an estimated best focus position and associated light adjusting systems are disclosed in U.S. Pat. Nos. 6,542,180 and 6,239,554, each incorporated herein by reference in its entirety. In addition, techniques for measuring surface contours are disclosed in U.S. Pat. No. 6,690,474, also incorporated herein by reference in its entirety.

Figure 1:
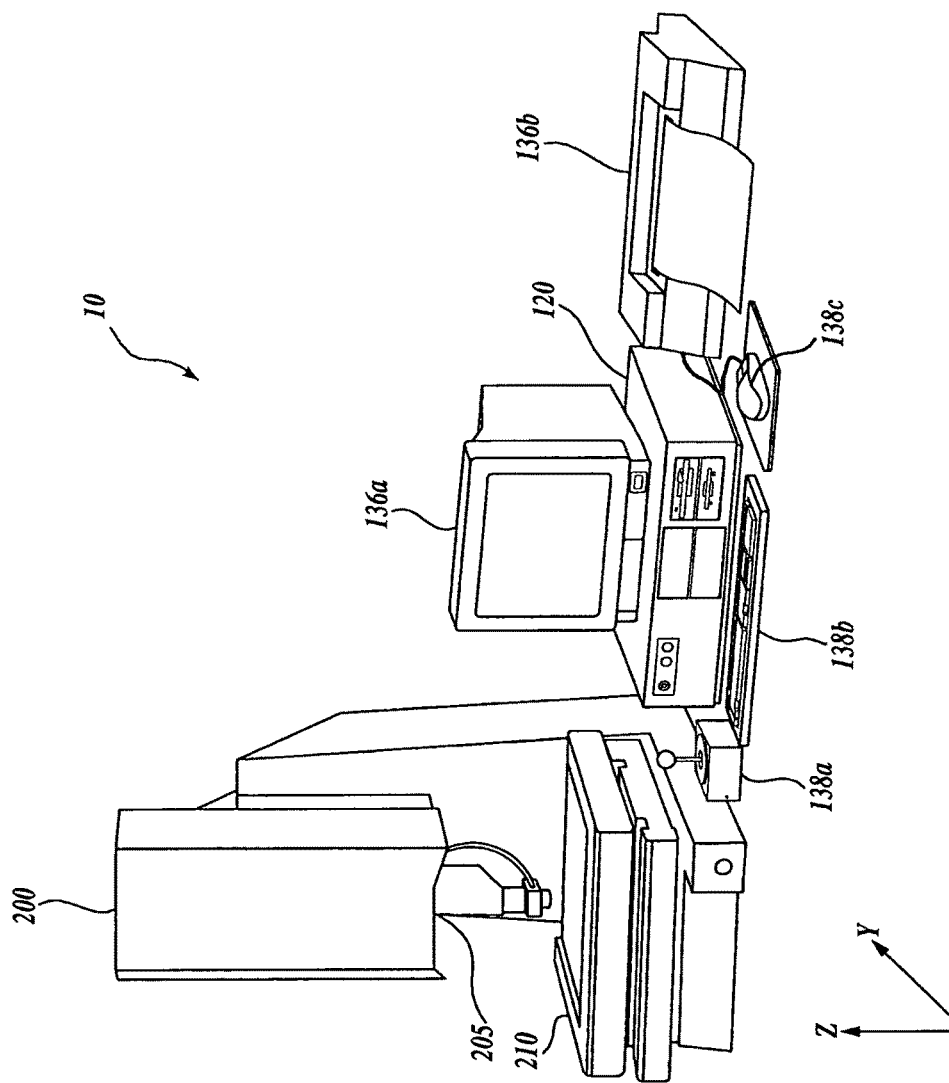
FIG. 1 shows a diagram of an exemplary general purpose machine vision inspection system.

FIG. 1 is a block diagram of an exemplary embodiment of a general purpose programmable machine vision inspection system 10 usable according to this invention. The machine vision inspection system 10 may include a vision measuring machine 200 that may be operably arranged to exchange data and control signals with a control system portion 120.

The control system portion 120 may be further operably arranged to exchange data and control signals with at least one of a monitor 136a, a printer 136b, a joystick 138a, a keyboard 138b, and a mouse 138c. The vision measuring machine 200 may include a moveable workpiece stage 210 and an optical imaging system 205, which may include a zoom lens or a number of interchangeable lenses. The zoom lens or interchangeable lenses may generally provide various magnifications for images produced by the optical imaging system 205.

The joystick 138a may be used to control the movement of the movable workpiece stage 210 in both X- and Y-axes horizontal directions, which may be generally parallel to the focal planes and perpendicular to the Z-axis movement direction of the optical imaging system 34. Frequently, Z-axis movement may be controlled by a rotary deflection component of a handle or knob of the joystick 138a. The joystick 138a may be provided in a form other than that shown, such as any visual representation or widget on the monitor 136a that may be intended to function as a "virtual motion control device" of the machine vision inspection system 10 and is controllable through any computer input device, such as the mouse 138c or other analogous devices.

Figure 2:
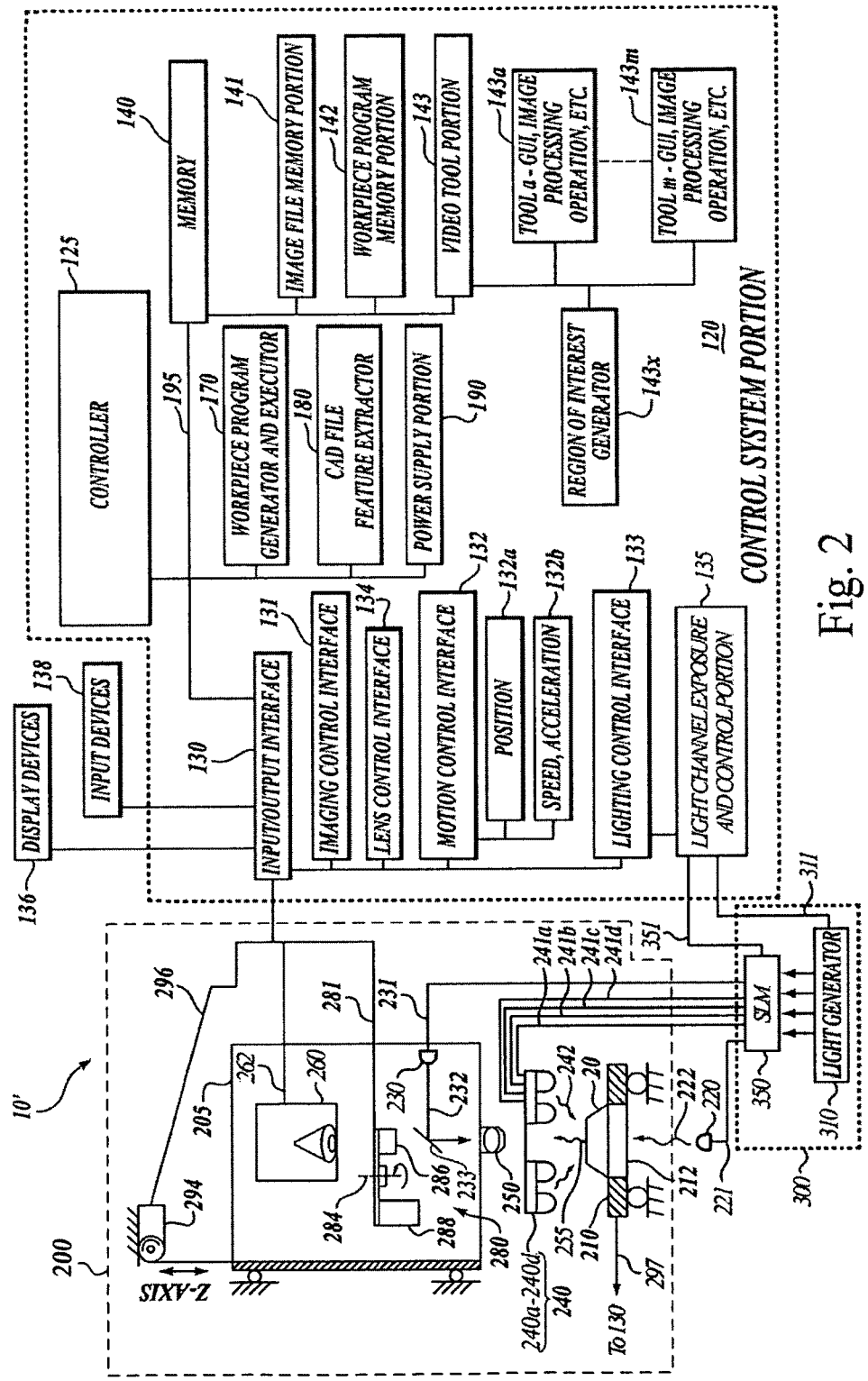
FIG. 2 shows a block diagram in greater detail of a control system, a vision components system and a light source system of the exemplary machine vision inspection system.

FIG. 2 shows a detailed block diagram of a machine vision inspection system 10', which is an exemplary embodiment of the machine vision inspection system 10, that includes the control system portion 120, the vision measuring machine 200 and, in addition, includes a controllable light generation system 300. The control system portion 120 may be arranged to exchange data and control signals with both the vision measuring machine 200 and the light generation system 300.

The control system portion 120 may include a controller 125 that may be in communication with, or connected to, an input/output interface 130, a memory 140, a workpiece program generator and executor 170, a computer-aided design (CAD) file feature extractor 180 and a power supply portion 190. The control system portion 120 may also be arranged to exchange data and control signals with display devices 136 and input devices 138, for example, through the input/output interface 130.

The input/output interface 130 may comprise an imaging control interface 131, a motion control interface 132, a lighting control interface 133, and a lens control interface 134. The motion control interface 132 may include a position portion 132a and a speed and acceleration portion 132b. The lighting control interface 133 may include lighting channel exposure and control portion 135.

The various elements of the control system portion 120 may generally encompass hard-wired circuits, software circuits, subroutines, objects, operations, application programming interfaces, managers, applications, or any other known or later-developed hardware or software structure. The display devices 136 may include, for example, the monitor 136a and the printer 136b (FIG. 1). The input devices 138 may include, for example, the joystick 138a, the keyboard 138b and the mouse 138c (FIG. 1). In general, the various elements of the control system portion 120, may be operably connected to each other and to external devices by any suitable known or later-developed power and/or signal busses, wireless communication signals, and/or application programming interfaces, or the like. Such interconnections are generally indicated by various interconnection lines 195, throughout the control system portion 120, in an arrangement of interconnections that is exemplary only, and not limiting.

The light generation system 300 may include one or more light generator 310 and a spatial light modulator (SLM) 350 to control the distribution of light from the light generator 310, to a plurality of light channels, as described further below. The light generator 310 and the SLM 350 may be arranged to exchange data and control signals with the light channel exposure and control portion 135, for example, by respective power and signal lines 311, 351. At least one of the lamps (not shown) of the light generator 310 may be used in a strobe illumination mode of operation to provide a combination of a very fast light generator response time (in the μs or ns range) and suitable optical power levels. In various exemplary embodiments, the light generator 310 may include a high intensity Xenon (Xe) flashlamp. However, in general, any light generator that emits a wavelength within a sensing range of the camera 260 may be used. Various features of the light generation system 300 are described further below.

The vision measuring machine 200 may include an optical assembly 205, light sources, including stage light source 220, coaxial light source 230, and programmable ring light (PRL) source 240. The workpiece stage 210 may include a central transparent portion 212 through which light from the stage light source 220 passes. The stage 210 may be controllably movable along X- and Y-axes that lie in a plane substantially parallel to the surface of the stage 210 where a workpiece or target 20 may be positioned.

The stage light source 220 may receive light through a light cable 221 from a respective channel of the SLM 350 to transmit light 222 through the transparent portion 212. The components that provide the light 222 may be regarded as a first light channel of the machine vision inspection system 10'. The coaxial light source 230 may receive light through a light cable 231 from a respective channel of the SLM 350 to transmit light 232 to a beamsplitter that provides a coaxial mirror 233 that directs the transmitted light 232 through the objective lens 250. The components that provide the light 232 may be regarded as a second light channel of the machine vision inspection system 10'. The programmable ring light (PRL) source 240 may form an annular ring above and around the workpiece 20 to transmit light 242 to the workpiece 20 at controllable angles. An exemplary configuration for the PRL source 240 may include four ring-light sources 240a through 240d, arranged in respective quadrants around the ring-light.

The four sources 240a through 240d may receive light through respective light cables 241a through 241d from respective channels of the SLM 350. The various light cables may comprise optical fiber bundles, or the like. The PRL source 240 may be formed as a combination of individually controllable sources. The components that provide respective portions of the light 242 may be regarded as four additional light channels of the machine vision inspection system 10'.

The workpiece 20 may be disposed on the stage 210 at a known or learned position. By detecting macroscopic positions of the stage 210 and/or the workpiece 20, the control system portion 120 may accurately determine where to capture workpiece images to perform inspection of various workpiece features.

The memory 140 may comprise an image file memory portion 141, a workpiece program memory portion 142, and a video tool portion 143. The video tool portion 143 may comprise a region of interest generator 143x, and various respective video tools 143a through 143m, which may include respective GUI interfaces, image processing operations, and the like, which assist a user in performing and/or programming various inspection operations. The region of interest generator 143x provides operations that may assist the user in defining desired regions of interest to be analyzed or operated upon be the various video tools 143a-143m, as described in the '180 patent, for example.

The memory 140 may store data and/or "tools" usable to operate the machine vision inspection system 10 to capture or acquire an image of the workpiece 20 with desired image characteristics. The memory 140 may further store data and/or video tools usable to operate the machine vision inspection system 10 to perform various inspection and measurement operations on the acquired images, either manually or automatically, and to output the results, for example, through the input/output interface 130 through data and/or control busses and/or the controller 125. The memory 140 may also contain data defining a GUI operable through the input/output interface 130 by way of data and/or control busses and/or the controller 125.

The optical assembly 205 may include, for example, a camera or image acquisition device 260, an interchangeable objective lens 250, a turret lens assembly 280, and the coaxial light source 230. The objective lens 250 and the camera 260 may be aligned along a camera axis. The optical assembly 205 may be controllably movable along the Z-axis that is generally orthogonal to the X- and Y-axes, for example, by using a controllable motor 294. Each of the X-, Y- and Z-axes of the machine vision inspection system 10 may be instrumented with respective X-, Y- and Z-axis position encoders (not shown) that provide spatial position information to the control system portion 120, for example, over suitable signal and/or control lines (not shown). The camera 260 may include a charge-couple diode (CCD) array, or a CMOS array, or any other suitable detector array, to provide an image based on the light received from the workpiece 20.

The turret lens assembly 280 may include two or more respective lenses 286, 288 that may be rotated around a rotation axis 284 to be respectively positioned in the optical path between the camera 260 and the objective lens 250 to provide a respective image magnification in combination with the objection lens 250. The control system portion 120 may rotate the turret lens assembly 280 to provide a desired image magnification. The input/output interface 130 may exchange data and control signals with the camera 260, the turret lens assembly 280 and the motor 294, for example, by power and signal lines or busses 262, 281, 296. Respective signal and/or control lines (not shown) of the respective X-, Y- and Z-axes position encoders (not shown) may also be in communication with the input/output interface 130. In addition to carrying image data, the signal line 262 may carry various signals from the controller 125 that set an image acquisition pixel range for the camera 260, initiate an image acquisition camera operation sequence, and/or similar operations.

The optical assembly 205 of the machine vision inspection system 10 may include, in addition to the previously discussed components, other lenses, and/or other optical elements, such as apertures, beam-splitters and other analogous devices, such as may be needed for providing desirable machine vision inspection system features.

The workpiece 20 to be imaged and inspected using the machine vision inspection system 10 may be placed on the stage 210. One or more of the light sources 220, 230, 240 may emit the respective light 222, 232, 242, that may illuminate the workpiece 20. Light may be reflected from or transmitted through the workpiece 20 as workpiece light 255, which may pass through the interchangeable objective lens 250 and one of the lenses 286, 288 of the turret lens assembly 280 to be received by the camera 260. The image of the workpiece 20, captured by the camera 260, may be output, for example, through the signal line 262 to the control system portion 120.

A distance between the stage 210 and the optical assembly 205 may be adjusted to change the focus of the image of the workpiece 20 captured by the camera 260. For example, the optical assembly 205 may be movable in the vertical (Z-axis) direction perpendicular to the stage 32, for example, using the controllable motor 294 that may drive an actuator, a connecting cable, or other analogous devices, to move the optical assembly 205 along the Z-axis. The term Z-axis, as used herein, refers to the axis for focusing the image obtained by the optical assembly 205. The controllable motor 294, when used, may be in communication with the control system portion 120, for example, through the signal line 296.

The control system portion 120 may be usable to determine image acquisition settings or parameters and/or acquire an image of the workpiece 20 with desired image characteristics in a region of interest that includes a workpiece feature to be inspected by workpiece program instructions. Such workpiece imaging instructions may be encoded by the workpiece part programming generator and executor 170 and transmitted to other components through data and/or control busses and/or application programming interfaces 195. The display devices 136 and input devices 138 may be used to view, create and/or modify part programs, to view the images captured by the camera 260, and/or to view and/or modify various GUI features for monitoring and/or controlling the machine vision inspection system 10'. The physical movements may be controlled by the motion control interface 132.

To achieve control of the physical movements of the camera 260, the motion control interface 132 may receive position information from the X-, Y- and Z-axis position encoders and may transmit position altering control signals via data and/or control busses and/or application programming interfaces 195. In general, such instructions may cause the machine vision inspection system 10' to manipulate the stage 210 and/or the camera 260 such that a particular portion of the workpiece 20 may be within the field of view of the camera 260 and may provide a desired magnification, a desired focus state and an appropriate illumination. This process may be repeated for each of multiple images in a set of images that are to be captured for inspecting the workpiece 20.

Figure 3:
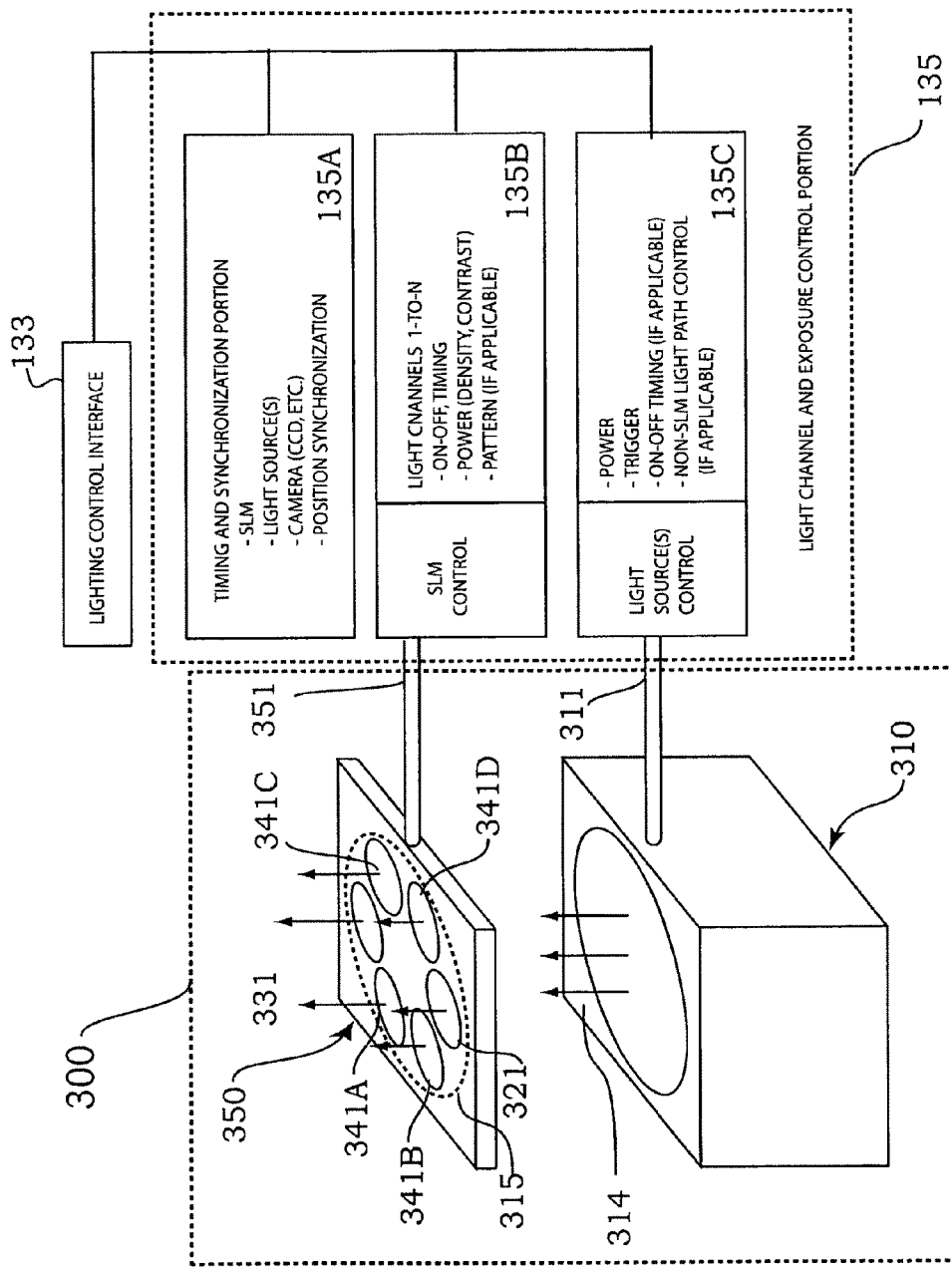
FIG. 3 shows a block diagram in greater detail of the light source system and a lighting control interface.

FIG. 3 shows an exemplary block diagram of details of the lighting control interface 133 including the light channel and exposure control portion 135, and the light generation system 300. The light channel and exposure control portion 135 may include a timing and synchronization portion 135a, an SLM control portion 135b and a light generator control portion 135c. The SLM control portion 135b may be connected to the SLM 350, for example, through a signal line or buss 351. The light generator control portion 135c may be connected to the light generator 310, for example, through a power and/or signal line or buss 311.

The light generator 310 may emit light 314 to illuminate an illumination area 315 on the SLM 350. The SLM 350 may generally transmit, partially transmit, or block light. The SLM 350 may include a plurality of respective controllable apertures within the illumination area 315. The respective apertures may generally provide illumination control for the respective light channels of the machine vision inspection system by transmitting, partially transmitting, or blocking the light 314 to each of the respective light channels. In the example shown in FIG. 3, the apertures include a stage light channel aperture 321, a coaxial light channel aperture 331, and PRL light channel apertures 341a, 341b, 341c, 341d. The respective apertures 321, 331, 341a-341d may individually control the amount of light 314 transmitted to the respective light cables 221, 231, 241a-241d (FIG. 2) to be output through the respective light sources 220, 230, 240a-240d.

The SLM 350 may include an arrangement of shutters that provide the respective apertures. The shutters may be of any now-known or later-developed type that can provide controllable light transmitting and light blocking functions in a desired pattern. In various embodiments, it may be advantageous if the shutter may also be used to partially-transmit light. For example, such that the SLM may be used to selectively transmit, attenuate and/or block light from the light generator 310. One example of such an SLM may be a microdisplay graphics array from CRL-Opto in Dunfermline, Scotland, United Kingdom, which includes an LCD pixel array that may generally be controlled by conventional video signals, if desired, and may be used to display an electronically generated 8-bit gray-scale pattern that may transmit, partially-transmit, or block the light 314 through any given pixel of the pattern, depending on its gray-scale value. In such a case, the various respective apertures may be implemented as features of the pattern, and the pattern may be controlled at conventional video rates. Alternatively, a custom LCD including a custom pattern of desired apertures may be used in various embodiments. It should be appreciated that the SLM 350 allows one light generator 310 to provide independently controllable lighting to a plurality of light channels, while also allowing the light from a plurality of light channels to be perfectly synchronized, for example as one light generator 310 is strobed during an image acquisition. The use of one light generator 310 also allows reduced cost and reduced size, relative to the use of an individual light generator for each light channel, for example.

Alternatively, the SLM 350 may include an arrangement of any now-known or later-developed type of controllable reflective shutters that can provide controllable light deflection in a desired pattern. In such a case, the light generator 310 may be arranged such that the light 314 will not reach the various light channels unless the controllable reflective shutters or pixels "transmit" the light by reflecting and/or deflecting light at a specific angle toward the various light channels. For example, in contrast to FIG. 3, the reflective SLM may be nominally oriented along a plane at 45 degrees relative to the light 314, and the reflective array elements may be aligned along that plane to transmit the light 314 toward the various respective light channels by reflecting and/or deflecting it at a right angle to reach the various respective light channels. To effectively "block" the light 314 from reaching the various light channels, the reflective array elements or pixels may be disabled from reflecting the light 314 at right angles, either by altering their individual angles, of by blocking their individual reflective light paths, for example using individually controllable LCD blocking elements. Examples of controllable reflective shutter arrays that may be used include liquid crystal on silicon (LCOS) micro-display products, for example, from CRL Opto, Dunfermline, Scotland, and digital light projector (DLP) micro-mirror products, for example, from Texas Instruments DLP Products, Plano, Tex. In such a case, the various respective apertures may be implemented as features of a reflective pattern, and the pattern may be controlled at conventional video rates. Although the micro-mirror type of devices may not provide partially-transmitting pixels, it will be appreciated that a light channel aperture implemented using a micro-mirror device may alternatively attenuate the light transmitted to a particular light channel by effective reducing the its aperture size, as needed. For example, the aperture diameter may be reduced by altering the configuration of the pixels that form the aperture.

As previously outlined, it may be advantageous if at least one of the lamps of the light generator 310 may be used in a strobe illumination mode of operation to provide a combination of a very fast light generator response time (in the μs or ns range) at suitable optical power levels. Such illumination is particularly advantageous for allowing imaging of workpieces while continuing to move the stage 210 (FIG. 2), which increases the throughput of the machine vision system 10'. One example of a light generator 310 may include one or more high intensity light emitting diodes (LEDs), such as one of the LEDs in the Luxeon™ product line, available from Lumileds Lighting, LLC, of San Jose, Calif., which may be used for both continuous wave (CW) and strobe illumination as described in the '351 patent. In various exemplary embodiments, a CW light source may include a high intensity discharge (HID) metal halide lamp and/or a quartz halogen lamp.

In various exemplary embodiments, the strobe light generator may include a high intensity Xenon (Xe) flashlamp, such as model CX-1500 Xe flashlamp of the CX-Strobe™ series from PerkinElmer® Optoelectronics of Fremont, Calif. The CX-1500 Xe flashlamp may illuminate across an electromagnetic spectrum for wavelengths between 250 nm and more than 1100 nm. In various embodiments, it may be desirable to filter the light from the flashlamp, to reduce heating and/or chromatic aberrations. For example, the filter may pass the visible wavelength range between 390 nm (violet) and 750 nm (red) to the light channels. However, in various embodiments, other wavelengths ranges may be desired. The CX-1500 Xe flashlamp may cycle at a repeat rate of between 16 Hz and 35 Hz, with a pulse duration of between 8 μs and 10 μs. The CX-1500 Xe flashlamp may produce a radiometric output of 256 mJ and a photometric light output of 205 lumen-sec at 600 VDC that may be directed into a 0.9" (23 mm) diameter fiber optic guide.

It should be appreciated that a general purpose machine vision system may image a wide variety of workpieces, some of which may have surfaces with low reflectivity. Furthermore, magnified images may be desired. Furthermore, fast exposures, enabling imaging of moving workpieces may be desired. All of these factors tend to reduce the amount of light accumulated during an image exposure, as discussed further below. Thus, a very high intensity flashlamp may be advantageous for providing a very versatile machine vision inspection system.

The timing and synchronization portion 135a may provide operations that send and receive control signals that synchronize the SLM 350, the light generator 310, the camera 260 and positioning of the machine vision inspection system 10'. The SLM control portion 135b may provide control for the various light channels by controlling the on-off timing, contrast, and aperture pattern, if applicable, of the SLM 350. The light generator control portion 135c may provide control for the power levels, the trigger signals, and on-off timing (if applicable) of the one or more lamps or LED's, or the like, of the light generator 310. The light generator control portion 135c may also provide for light path control for auxiliary light sources (if applicable), as outlined further below.

Figure 4:
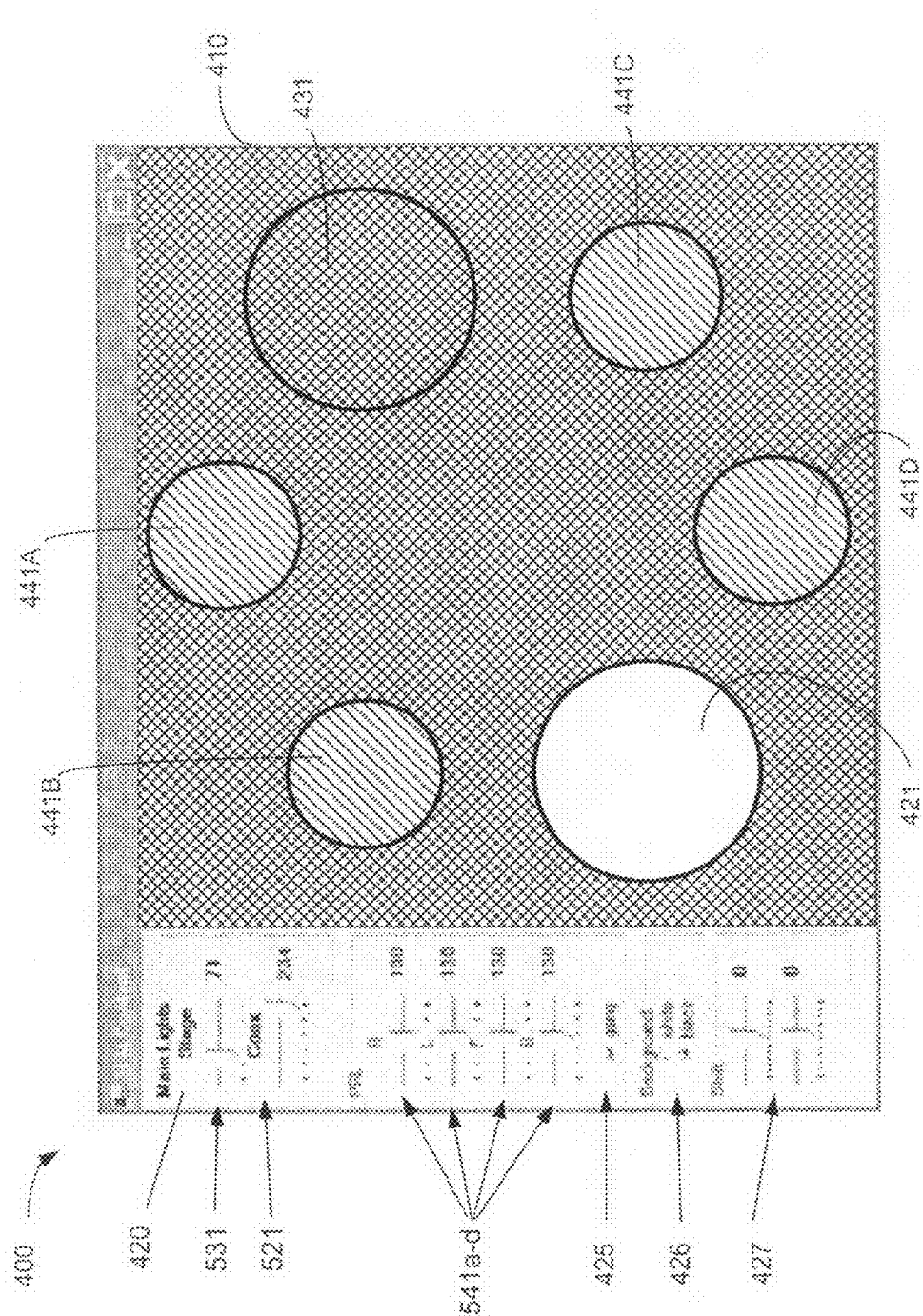
FIG. 4 shows an exemplary graphical user interface of a control for a spatial light modulator.

FIG. 4 shows an exemplary SLM setup and control GUI 400 including an SLM image field 410 and a control window 420. The SLM image field 410 shows one exemplary aperture pattern including a stage light channel aperture representation 431, a coaxial light channel aperture representation 421, and PRL light channel aperture representations 441a, 441b, 441c, 441d. The respective aperture representations may correspond to the apertures 321, 331, 341a-341d of the SLM 350, for example. The control window 420 includes a stage light channel aperture control 531, a coaxial light channel aperture control 521, and PRL light channel aperture controls 541a, 541b, 541c, 541d, which control the similarly numbered aperture representations, and a set of corresponding control signals that may be implemented to control the SLM 350. For example, when the SLM 350 is an LCD pixel array, the pixel array may be controlled such that the gray-scale values that control the pixel array correspond to the gray-scale values of the pixels shown in the SLM image field 410.

For the example shown in FIG. 4, the double cross-hatched background represents a light-blocking region of the SLM 350. The stage light channel aperture representation 431 shows a similar double cross-hatching to represent a significantly light-blocking setting of the corresponding control 531. The coaxial light channel aperture representation 421 shows an unfilled area to represent a significantly light-transmitting setting of the corresponding control 521. The PRL light channel aperture representations 441a, 441b, 441c, 441d, show single cross-hatching to represent a partially light-transmitting setting of the corresponding controls 541a, 541b, 541c, 541d. The layout of the aperture representations 421, 431, and 441a-441d in the SLM image field 410 may correspond directly to a physical layout of the apertures 321, 331, and 341a-341d of the SLM 350, and to a physical layout of the input ends of the light cables 221, 231, and 241a-241d (FIG. 2), which may be held in a fixture proximate to the SLM 350, such that they are properly aligned to receive transmitted light from the corresponding apertures. The particular layout shown in FIG. 4 is exemplary and is not limiting. Other configurations are possible and contemplated. It will be appreciated that the various aspects of aperture control described above with reference to FIG. 4, may also generally be provided under manual, semi-automatic, or automatic control as functions of the SLM control 135b. Accordingly, these and other manual, semi-automatic, or automatic control measures over the apertures 321, 331, and 341a-341d of the SLM 350 may be implemented to support various learn mode and/or run mode operations of the machine vision inspection system 10'.

The control window 420 may include panels with the "slider" controls outlined above, along with corresponding numerical settings, along with other slider controls, numerical displays and radio buttons to adjust and display selected parameters which may control the light intensities of the various lighting channels and their representations in the SLM image field 410. The PRL panel may include a "gang" PRL radio button 425 that indicates whether the PRL sources

240*a* through 240*d* are ganged together, i.e., adjusted to the same setting, rather than separately controlled.

The slider control scales may denote the range (from none to full) of the intensity to be transmitted by the corresponding aperture. The slider control pointer and the numerical display may indicate the selected value to which the respective light source intensity may have been set. The numerical display may denote a digital quantity across a binary integer grayscale range of $2^8$ from full illumination at 255 to no illumination at 0. In the example illustrated, the stage control panel 531 shows, for example, a low-level value of 71, the coaxial control panel 521 shows, for example, a high-level value of 234, while all the PRL control panels 541*a-d* show, for example, a mid-level value of 130. The PRL radio button 425 shows, for example, that the PRL sources are ganged together in this example.

A background radio button 426 may indicate a selection of the display background, being either white or black, shown in the example as being black (double cross-hatched.) In a set-up mode of operation, the respective slider controls of "Shift" scales 427V and 427H may be used to adjust the position of the aperture pattern shown in the SLM image field 410 over a limited range along the vertical (V) and horizontal (H) directions, respectively. The actual location of the aperture pattern of the SLM 350 may be controlled in a corresponding manner. The alignment of the actual aperture pattern of the SLM 350 relative to the physical layout of the input ends of the light cables 221, 231, and 241*a*-241*d* (FIG. 2), which may be held in a fixture proximate to the SLM 350, may be monitored by direct observation, or by monitoring a light transmission signal through the various light channels or the like, until the various apertures have been properly aligned to the various light cable using the "Shift" controls. Then the corresponding "calibration" settings may be stored in the SLM control 135*b*, for use during ongoing operations of the machine vision inspection system 10'.

Figure 5:
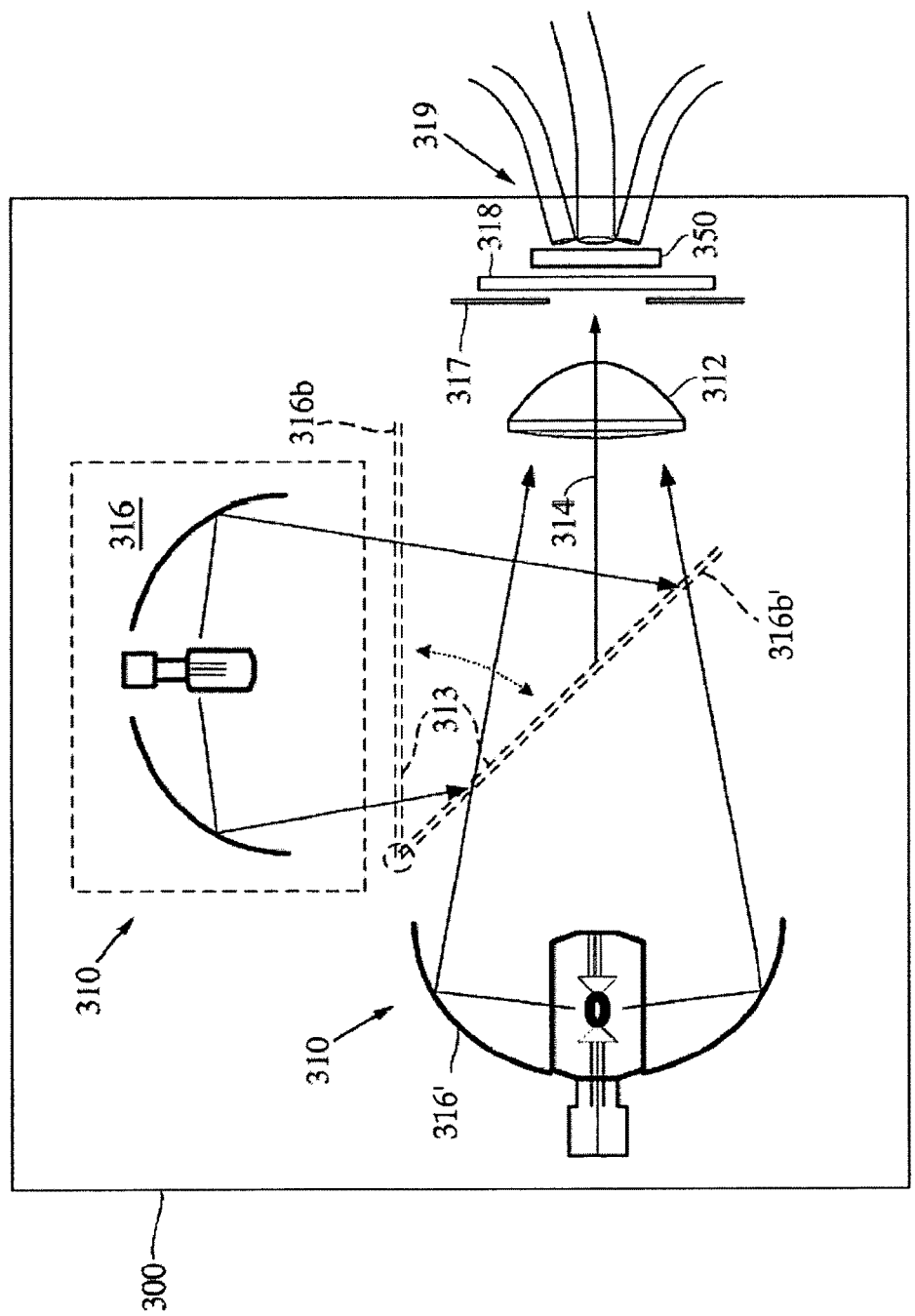
FIG. 5 shows a schematic layout diagram of exemplary lighting system including a spatial light modulator.

FIG. 5 shows an exemplary schematic layout diagram of the light generation system 300, including light generator(s) 310 and a spatial light modulator 350. A collimator lens 312 may receive light 314 from one of a CW lamp 316, such as an HID lamp, or a Xe strobe 316'. Both may have substantially elliptical mirrors. A hinged mirror 313 may pivot to enable either the HID lamp 316 or the strobe 316' to transmit light through the collimator lens 312. In a first position 316*b*, the light from HID lamp 316 is blocked by the mirror 313, and the Xe strobe 316' may shine directly into the collimator lens 312. In a second position 317*b*, the light from Xe strobe 316' is blocked by the mirror 313, and the light from HID lamp 316 may be reflected into the collimator lens 312.

Figure 9:
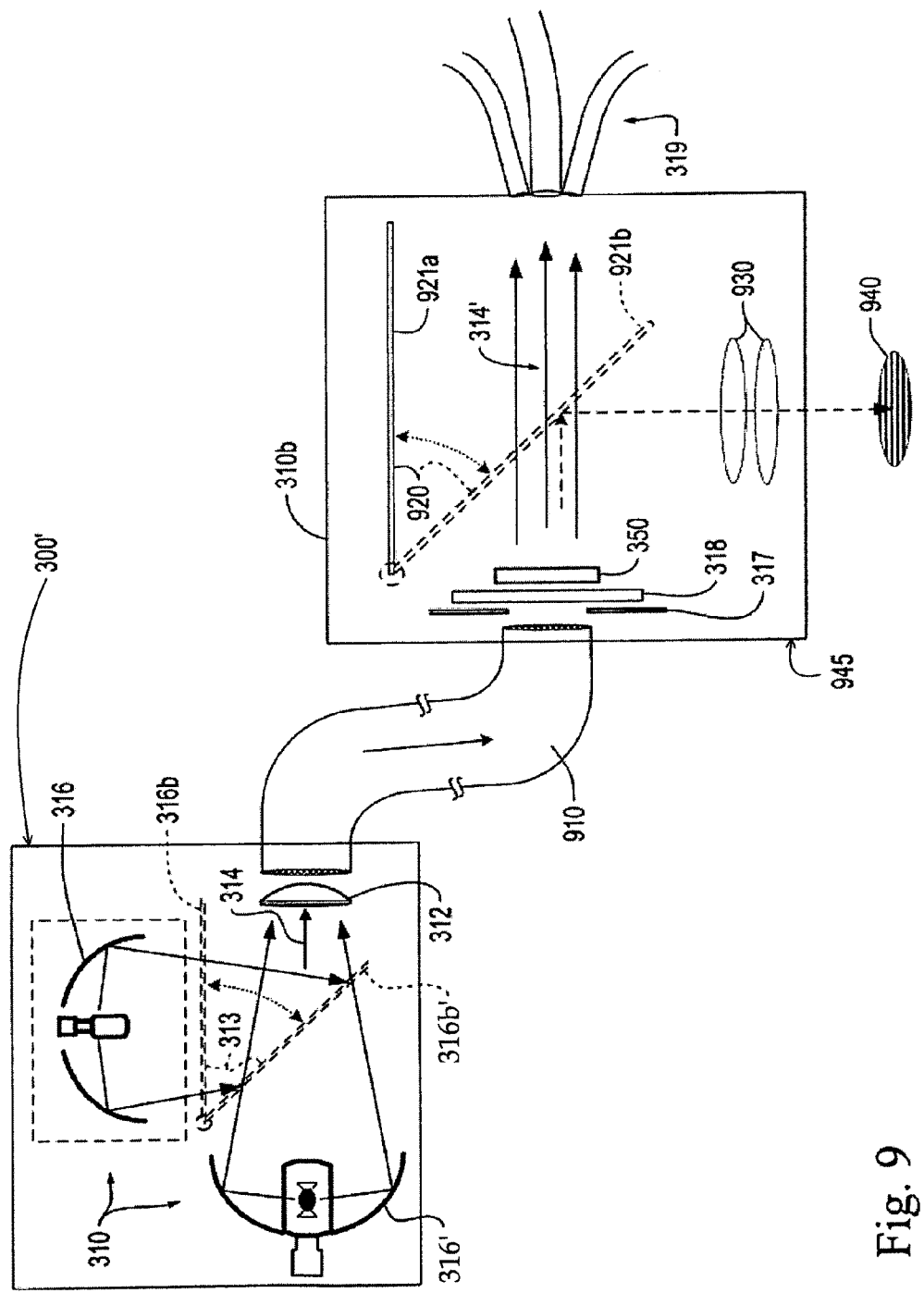
FIG. 9 shows a schematic layout diagram of exemplary light channels, including a structured light channel and a spatial light modulator.

In either case, a light 314 may pass through the collimator lens 312, and be directed as collimated, or approximately collimated, light toward the SLM 350. In the example shown in FIG. 5, the light 314 may pass through an aperture 317, which may define the illumination area 315 (FIG. 3), and may then pass through a filter 318 to block wavelengths that may contribute deleterious effects, such as undesirable heating, or image blur, or the like. For example, in some applications, wavelengths in the ultraviolet portion of the electromagnetic spectrum may focus differently than a dominant imaging wavelength and degrade images. The light may then pass, for example, through the previously discussed respective apertures of the SLM 350 and into the respective optical cables of the optical cable arrangement 319 that are aligned with the respective apertures, to be transmitted to the respective positions of the illumination sources 220, 230, and 240, for example. The input ends of the optical cables of the optical cable arrangement 319 may be inserted into an alignment and mounting plate (not shown) that has a plurality of holes that receive the ends of the optical cables and hold them in an alignment that matches the aperture pattern of the SLM 350. The mounting plate may be mounted proximate to, or flush to, the SLM 350, and may also act as an optical baffle or barrier between the outputs of the various apertures and the optical cable ends, to reduce stray light "cross talk" between the light channels. An alternative configuration is shown in FIG. 9, described below.

Figure 6:
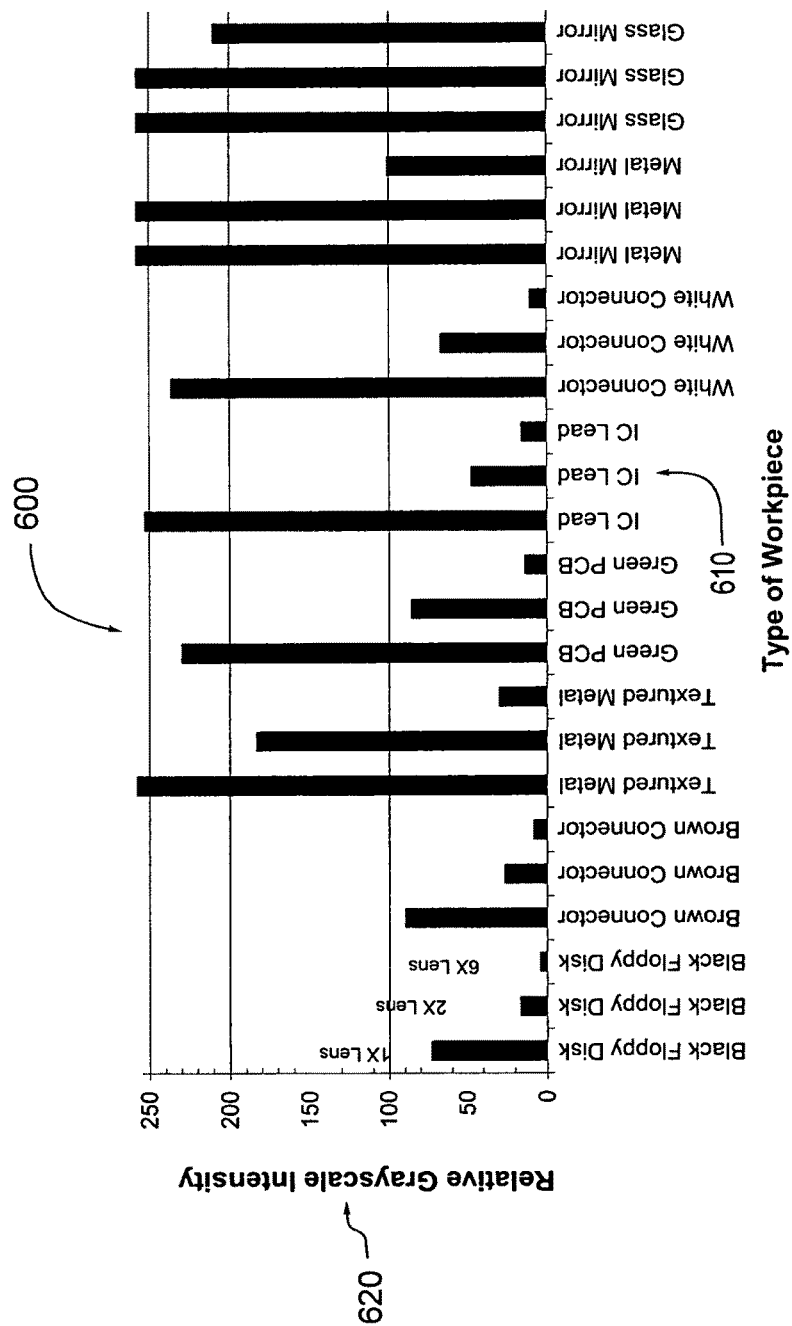
FIG. 6 shows a bar-chart of exemplary relative grayscale intensities obtained when imaging various materials at different magnifications.

FIG. 6 shows an exemplary bar chart 600 for the relative average grayscale intensity observed using a typical camera and constant illumination, for sundry workpiece surfaces at specific magnifications. Several materials, each at 1×, 2× and 6× magnification are listed along the abscissa 610, including floppy disk, brown connector, textured metal, green printed circuit board (PCB), integrated circuit (IC) lead, white connector, metal mirror and glass mirror. The 8-bit relative average grayscale intensity along the ordinate 620 ranges from 0 through 255, where zero is no intensity and 255 represents camera saturation or overexposure.

As may be observed from the bar chart, increases in magnification reduce the amount of gathered light and the photographic exposure, and generally would demand greater quantities of light to provide sufficient photographic exposure. Also, darker materials, such as the floppy disk may require far greater quantities of light than brighter materials, such as the white connector, or specularly reflective materials, such as the mirrors. This difference in the amount of exposure light received for various materials and magnification demonstrates that the light levels that may be required for imaging and inspection of various magnified surfaces in a general purpose machine vision inspection system may vary widely. In fact, if the saturation values shown for the low-magnification imaging of various materials are to be avoided, and if the low illumination values shown for the higher-magnification imaging of various materials are to be brought up to acceptable imaging levels, the illumination intensity may be required to be adjustable over a range of many orders of magnitude. Thus, there is a need for an illumination system that provides an extraordinarily wide dynamic range and precise control of available illumination.

To increase throughput, imaging the workpiece 20 disposed on the stage 210 may be performed while the stage 210 remains in motion. Under selected conditions of image magnification and stage speed, a strobe light flash of high intensity and short duration may be required to sufficiently illuminate the workpiece 20 in a short enough exposure time to avoid image blur during workpiece motion. To achieve a desirable illumination dynamic range with short illumination and/or exposure durations, an extremely bright strobe lamp, such as a Xe lamp, may be advantageous. For many types of lamps (which may also include LED's, or lasers, or the like, as the term "lamp" is used herein), after being triggered the strobe flash "profile" may temporally change in light intensity beginning with a gradual initial rise, followed by a rapid increase, a leveling off, a rapid reduction and a more gradual decay. Providing a reliable and consistent illumination exposure over a wide dynamic range using such a flash profile would be desirable.

Figure 7:
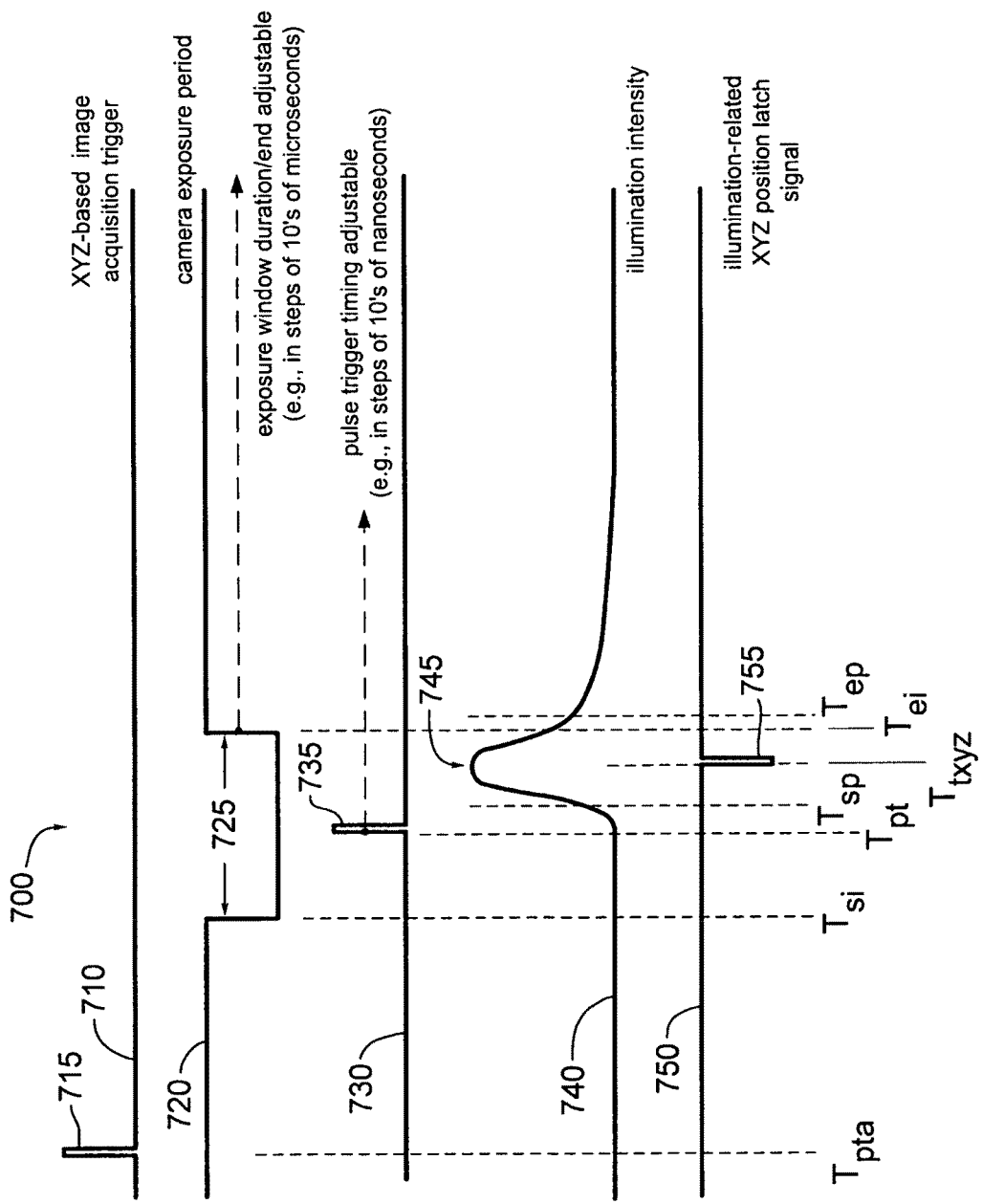
FIG. 7 shows a timeline chart corresponding to a first exemplary embodiment of signals for controlling a strobe pulse duration and a camera integration period associated with strobe illumination and exposure control.

FIG. 7 shows a timeline chart 700 corresponding to a first exemplary embodiment of signals (e.g. trigger signals) for controlling a strobe pulse duration and a camera integration period associated with strobe illumination and exposure control. The exposure level for an image may be determined by the transient light level integrated by the camera over an exposure duration. The effective image exposure time may generally be limited by the strobe duration, or, when CW illumination or "long" illumination pulses are used, by the camera integration period. However, it is one goal of precision machine vision inspection systems to provide highly consistent precision metrology images that do not vary from workpiece to workpiece, such that edge measurements and the like, which form the basis for precision inspection, do vary from workpiece to workpiece unless the workpieces truly vary. Thus, in order to mitigate the changes in effective duration of the decay portion from one strobe flash to another, resulting in unacceptable variation in the total image exposure illumination, it may be desirable to truncate the decay portion of the flash by ending the camera integration period at a consistent time within the flash period. Furthermore, it should be appreciated that with a Xe lamp, for example, the ability to vary the flash duration may be limited, and the flash duration may be inherently less than a typical minimum camera integration period. Therefore, methods to reduce the effective exposure illumination provided by a strobe flash, by orders of magnitude, with consistent control, may be desirable.

The chart 700 includes, for example, five timelines. The first timeline 710 represents an image acquisition trigger signal 715 beginning at a position trigger time $T_{pta}$ based on positional X-, Y- and Z-axis coordinates of the stage 210 (FIG. 2), which may correspond to a workpiece feature being positioned in the field of view of the camera 260.

The second timeline 720 represents a camera integration duration 725, that may have a programmable duration ($T_{ei}$-$T_{si}$) as short as tens of microseconds, and as long as several milliseconds. The controlled duration may be controlled based on a high-speed clock, such that it is relatively consistent. The camera integration duration 725 may start at integration begin time $T_{si}$ and end at integration end time $T_{ei}$. In some implementations, the integration begin time $T_{si}$ may occur a discrete latency period ($T_{si}$-$T_{pta}$) after the position trigger time $T_{pta}$ has been used to initiate a camera integration period. However, the latency period may be relatively consistent.

The third timeline 730 represents the flash initiation signal 735 beginning at a pulse trigger time $T_{pt}$ to initiate the strobe flash. In some implementations, the pulse trigger time $T_{pt}$ may be based by the same high-speed clock that is used to determine the camera integration duration 725. Therefore, a pulse trigger delay period ($T_{pt}$-$T_{si}$) may be programmable, based on the high-speed clock, and relatively consistent. The beginning of the pulse trigger time $T_{pt}$ may initiate the strobe pulse flash intensity profile indicated by the fourth timeline 740. The flash intensity may exhibit a transient profile, described further below, that rises to a peak 745 before diminishing.

The fifth timeline 750 represents an exposure-related coordinate position latch signal 755 beginning at latch time $T_{txyz}$ that may coincide with an effective or nominal exposure time. The X-, Y- and Z-coordinates for the stage 210 or the workpiece 20 at the latch time $T_{txyz}$ may be associated with the acquired image and may be stored in memory 140. Descriptions of the timeline events, listed in order of occurrence during an image acquisition cycle, are summarized in Table 1 below.

TABLE 1

| Event | No. | Time | Label |
| --- | --- | --- | --- |
| trigger image acquisition | 715 | position trigger acquisition | $T_{pta}$ |
| begin camera image integration ($T_{si}$ → $T_{ei}$) | 725 | start integration | $T_{si}$ |

TABLE 1-continued

| Event | No. | Time | Label |
| --- | --- | --- | --- |
| strobe flash initiation | 735 | pulse trigger | $T_{pt}$ |
| flash pulse start | | start pulse | $T_{sp}$ |
| flash peak intensity | 745 | | |
| position latch signal | 755 | xyz coordinate assigned to image | $T_{txyz}$ |
| end camera image integration ($T_{si}$ → $T_{ei}$) | | integration end | $T_{ei}$ |
| flash pulse end | | end pulse | $T_{ep}$ |

The strobe pulse flash intensity profile begins at the pulse trigger $T_{pt}$ with an initial gradual rise until effective start of the flash at time $T_{sp}$. After a rapid rise to a peak value 745, the flash may then diminish rapidly, to an effective end point of the flash at a time $T_{ep}$, and then continue to decay, providing little additional illumination energy, as shown in FIG. 7. For a particular implementation and an particular lamp, a latency period between the pulse trigger time $T_{pt}$ and the effective pulse start time $T_{sp}$ may be relatively consistent. Furthermore, for a given time period ($T_{ep}$-$T_{sp}$), the intensity profile and the illumination energy provided at a particular operating voltage for a particular lamp may be relatively consistent.

As previously indicated, with a Xe lamp, for example, the ability to vary the flash duration (or profile) may be limited, and the flash duration may be inherently less than a typical minimum camera integration period. Therefore, to reduce the effective exposure illumination provided by a strobe flash, by orders of magnitude, with consistent control, it may be desirable that the camera exposure end at a predictable and consistent time before the effective end time $T_{ep}$ of the flash. As previously indicated, the pulse trigger delay period ($T_{pt}$-$T_{si}$) may be programmable, based on the high-speed clock, and relatively consistent. Similarly, the programmable camera integration duration ($T_{ei}$-$T_{si}$) may be programmable, based on the same high-speed clock, and relatively consistent. Furthermore, the latency period between the pulse trigger time $T_{pt}$ and the effective pulse start time $T_{sp}$ may be relatively consistent. Therefore, for a given flash time period ($T_{ep}$-$T_{sp}$) and associated profile, the effective exposure illumination may be controlled by selecting and/or programming the programmable camera integration duration ($T_{ei}$-$T_{si}$) and the pulse trigger delay period ($T_{pt}$-$T_{si}$), such that camera integration end time $T_{ei}$ ends at a predictable time during the flash profile, and truncates and determines the effective image exposure illumination. That is, to control the effective image illumination over a wide dynamic range, the start of the effective image exposure illumination may begin with the flash, a short time following the start of the camera integration period, and may end with the end of the camera integration period, during the strobe flash profile. Of course, all of the above latency times may calibrated or determined for particular machines, lamps, voltage levels, etc., by design and/or experiment, and the results calibrated or stored such that a combination of timing, operating voltages, and the like, that provide a desired or calibrated illumination level may be readily determined.

Figure 8:
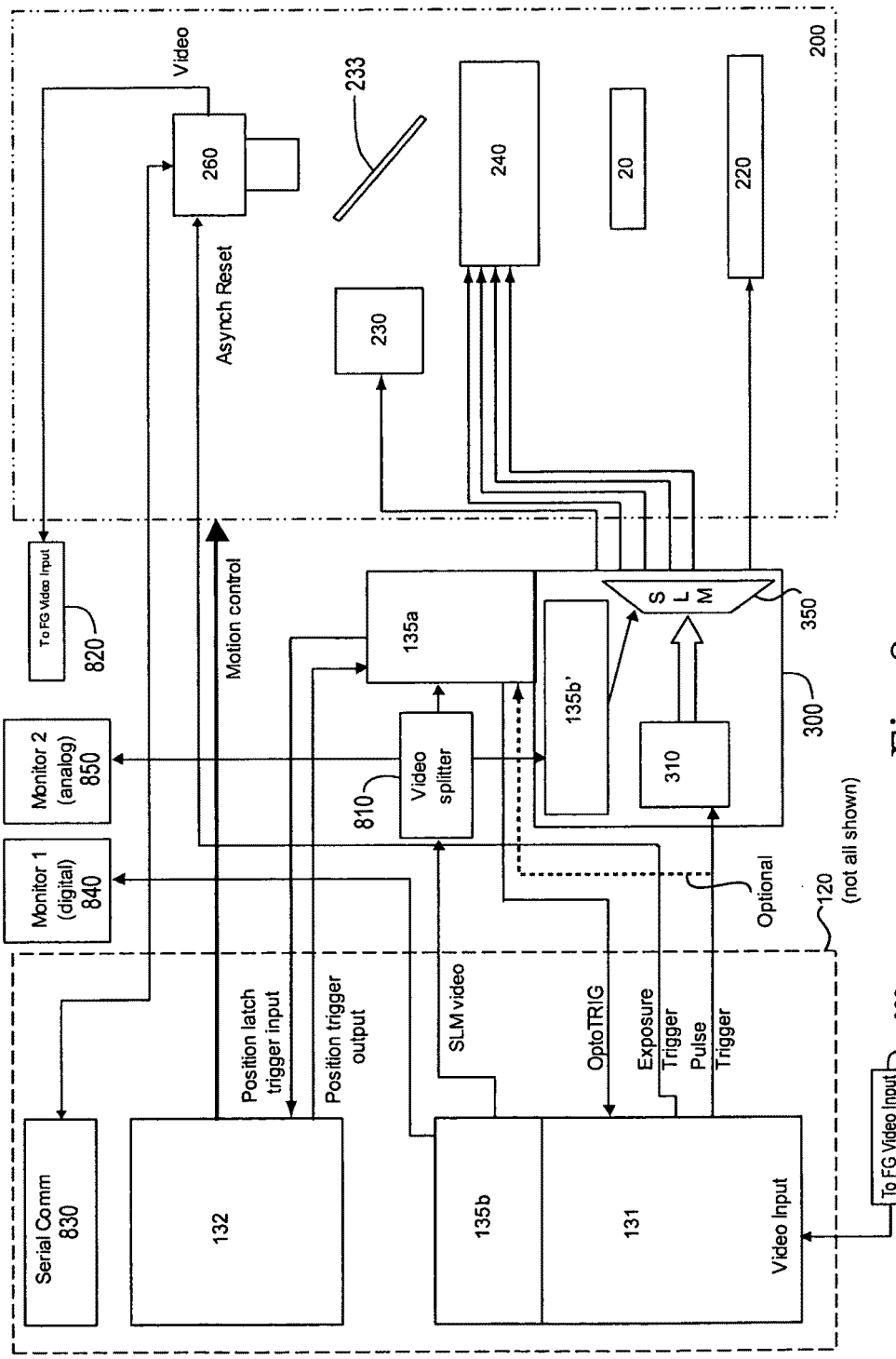
FIG. 8 shows a block diagram of an exemplary controller signals associated with a light generator and a vision measuring machine.

FIG. 8 shows an exemplary schematic block diagram including exemplary controller signals associated with portions of the control system portion 120, the vision measuring machine 200 and the light generation system 300, shown in FIGS. 2 and 3. The control system portion 120 includes the imaging control interface 131 that may comprise a framegrabber, the motion control interface 132, and the SLM control portion 135b (FIG. 3). The motion control interface 132 may comprise a motion controller. The light generation system 300 may include the light generator 310, the SLM 350 and an SLM interface portion 135b'. The timing and synchronization portion 135a may be located with, or packaged in, the light generation system 300, which may facilitate retrofit applications of the light generation system 300.

The light generation system 300 may operate in conjunction with the SLM control portion 135b, the timing and synchronization portion 135a (FIG. 3) and a video splitter 810. The timing and synchronization portion 135a and the SLM control portion 135b may be components of the light channel exposure and control portion 135 (FIG. 2). The vision measuring machine 200 (FIG. 2) includes the camera 260 and light sources 220, 230, 240 to illuminate the workpiece 20. The coaxial mirror 233 directs the light from the coaxial light source 230 toward the workpiece 20.

The camera 260 may receive signals from the imaging control interface 131, and may transmit image data via the imaging control interface 131 via a video input 820. The camera 260 may also receive and transmit signals between a serial communicator 830. A digital monitor 840 and/or an analog monitor 850 may display information related to the SLM 350 (for example, as one means to implement the SLM setup and control GUI 400, described with reference to FIG. 4). The SLM control portion 135b may supply SLM video signals to the video splitter 810 and the digital monitor 840. The video splitter 810 may supply video signals to the timing and synchronization portion 135a, and the SLM interface portion 135b', as well as with the analog monitor 850. For example, the video signal supplied to the SLM interface portion 135b' may be a conventional video signal, and the SLM interface portion 135b' may receive and decode the video signal into digital control signals suitable for operating an SLM 350 that may comprise an LCD pixel array, to produce a desired aperture configuration and operating state. Generally, such SLM interface decoders are commercially available from many vendors of LCD pixel array displays, such as the vendor of the LCD array previously described.

The timing and synchronization portion 135a may receive a position trigger output signal (for example, see 715, FIG. 7) from the motion control interface 132 (conventional motion controllers may be programmed to provide such position triggers) and relay a related signal to the imaging control interface 131 ("OptoTRIG" in FIG. 8) to maintain the timing relationships described with reference to FIG. 7. The imaging control interface 131 may supply an exposure trigger signal to the camera 260 to initiate the start of a camera integration period (for example, see 725, FIG. 7) and supply a pulse trigger (for example, see 735, FIG. 7) to the light generator 310, which may provide light to the SLM 350 for distribution to the light sources 220, 230, 240. The pulse trigger signal may be delayed relative to the exposure trigger signal by a programmable amount, based on a high speed clock included in the imaging control interface 131. This programmable delay, in conjunction with the programmed integration period of the camera 260 (and, possibly, various consistent timing latencies) may be used to control the effective image exposure illumination, as previously described with reference to FIG. 7. The high speed clock and the programmable integration period and pulse trigger signal delay may be implemented in various commercially available frame grabbers.

The timing and synchronization portion 135a may supply a position latch trigger signal (for example, see 755, FIG. 7) to the motion control interface 132, in order to latch the X-, Y- and Z-coordinates for the stage 210 or the workpiece 20 at a time that corresponds to the effective image exposure time. For example, the timing and synchronization portion 135a may implement a latching time that best corresponds to the effective image exposure time based on the known pulse trigger signal time and the known camera integration period, which allows the timing of the effective image exposure period (for example, see $T_{ei}$-$T_{sp}$, FIG. 7) to be known. For example, for short effective image exposure periods, it may be sufficient for the position latch timing to be set at the middle of the period ($T_{ei}$-$T_{sp}$). Or, for a more accurate effective image exposure time, the position latch time may be set at the intensity-weighted average time of the period ($T_{ei}$-$T_{sp}$), based on the known flash intensity profile, which may be determined experimentally, for example. The pulse trigger signal time that is used to determine the effective image exposure time may be determined internally to the timing and synchronization portion 135a, based on a delay related to the signal supplied to the imaging control interface 131 ("OptoTRIG" in FIG. 8), or, optionally, the pulse trigger signal time that is used may be determined based on sending the pulse trigger signal in parallel to the synchronization portion 135a, when it is sent to light generator 310.

Examples of selected components are described herein. The serial communicator 830 may represent an interface control tool. The control system portion 120 may include a personal computer backplane with the SLM control portion 135b provided by a Matrox dual video interface (DVI) daughter board and the imaging control interface 131 including a Corona II frame-grabber, both available from Matrox Electronic Systems Ltd, St-Régis Dorval (Québec), Canada. The vision measuring machine 200 may use QuickVision™ controls for controlling the various light sources. The SLM interface portion 135b' and the SLM 350 may be provided by a micro-display graphics array and associated electronics from CRL-Opto in Dunfermline, Scotland, United Kingdom. The motion control interface 132 may include a motion controller, for example one of the DMC-XXXX series of motion control cards commercially available from Galil Motion Control, Rocklin, Calif., or a motion control card such as that supplied as part of the previously described Quick Vision™ systems.

FIG. 9 shows a schematic layout diagram of an alternate configuration of the light generation system 300', including a light source channel that provides a structured light source 945. The light generation system 300' is generally similar to the light generation system 300 described with reference FIG. 5, therefore, only significant differences will be described. In a first portion, the light 314 is provided, as previously described with reference to FIG. 5.

The light 314 may be channeled, for example, through a fiber bundle light conduit 910 to then pass, as collimated light 314', through the aperture 317, the filter 318 and the SLM 350, which are located in a second portion of the light generation system 300'. The second portion of the light generation system 300' may include a hinged mirror 920, similar to the hinged mirror 313. In a first position 921a, the light 314' may shine directly into the previously described optical cable arrangement 319, to provide all of the previously described illumination functions.

Alternatively, the SLM 350 may be a controllable element that may include, or be configurable or programmable to form, a structured light pattern, in addition to the exemplary aperture patterns described above. For example, the structured light pattern may include a regular pattern of light (light transmitting) and dark (light blocking) stripes at a desired pitch, and may be formed using the previously described LCD pixel array. In such a case, the collimated light 314' that passes through the SLM 350 will may provide a field of parallel stripes of light. In a second position 921b, the hinged mirror may deflect the parallel stripes of light to pass through focusing and/or magnifying, and/or collimating lenses 930 before being emitted to provide a structured light source 945 that may be used to illuminate the workpiece 20 (FIG. 2). The structured light source 945 may be mounted at a fixed and/or known position to emit the parallel light stripes toward the workpiece 20 along an axis that is arranged at a known angle relative to the optical axis of the machine vision inspection system 10'. Thus, an image 940 of the structured light pattern on the surface of the workpiece 20 may be used in conjunction with known structured light triangulation techniques to determine relative dimensions of the profile of the workpiece 20 along the Z-axis direction. Various related teachings regarding the use of LCD arrays and structured light techniques are included in U.S. Pat. No. 6,690,474, which is incorporated herein by reference in its entirety.

It should be appreciated that in embodiments where the SLM 350 may be implemented such that the various respective channel apertures may be partially transmitting, for example, when the previously described LCD pixel array is used, the SLM 350 may advantageously be used to increase the dynamic range of the effective image exposure illumination. That is, in addition to the dynamic range control provided by the previously described measures of controlling the camera integration period and the strobe flash timing, gray-level control of an LCD pixel array, or a custom LCD element, or the like, may be used in parallel with any of the foregoing techniques, to provide additional illumination dynamic range.

Table 2 shows various factors which may be used in various combinations to provide a desired illumination level, including the use of a partially-transmitting type of SLM. Row 1 shows that an LCD pixel array may provide a variable illumination attenuation that may be controlled with an 8-bit gray-level command. However, in practice, the actual level of variation observed in the transmitted light is limited to approximately 150:1. Row 2 shows that an LCD pixel array may provide a variable "brightness" attenuation that affects all pixels at once, and may provide an actual level of variation observed in the transmitted light that is approximately 1.2:1. Row 3 shows that a Xe strobe lamp may provide a variable "brightness" depending on its operating voltage level, and may provide an actual level of variation observed in the provided and transmitted light that is approximately 17:1. Row 4 shows that a Xe strobe lamp generally provides an effective exposure time that is shorter than a typical minimum camera integration period, therefore, for strobe exposures, the overall duration of the camera exposure period is not used to affect the exposure. However, as previously indicated, the pulse duration may be set so as to stop the image exposure to effectively truncate part of the flash profile. Row 5 shows that the pulse trigger delay (for example, see $[T_{pt}\text{-}T_{si}]$, FIG. 7), which governs the relative timing between the camera integration period and the flash profile, may be adjusted in 40 ns time steps. That is, the flash profile may be selectively eliminated from the image exposure, in 40 ns time steps. In practice, the actual level of variation observed in the transmitted light by using this control measure may be approximately 250:1. Rows 6 and 7 show factors which may vary from machine to machine, lamp to lamp, etc. Generally, it may be desirable to calibrate and/or compensate these variations. Overall, according to Table 2, all of these techniques may be used in combination to provide an effective image exposure illumination dynamic range of approximately 765,000:1 in a set of relatively precisely controlled and repeatable increments.

TABLE 2

| | Item | Adjustment Setting | Adjustment steps | Units | Actual effect on exposure | Control Level |
|---|---|---|---|---|---|---|
| 1 | Pixel brightness (SLM) | 0-255 (8 bit) | DN | | 150:1 | Individual light channels (Individual Pixels of SLM) |
| 2 | Display brightness (SLM) | 0x00-0x80 | DN | | 1.2:1 | All Light Channels together (Entire SLM at once) |
| 3 | Xe brightness (flash lamp) | 150-600 | Volts | Volt | 17:1 | All Light Channels together |
| 4 | CCD exposure (Tei-Tsi) | 0.1-250 | 10's of μs (but stable and repeatable) | time | None | All Light Channels together (Entire camera at once) Note: No effect for strobe exposures. Strobe pulse timing controls effective exposure time. |
| 5 | Pulse trigger delay (Tpt-Tsi) | 0-250 | 40 ns time steps | time | 250:1* | All Light Channels together |
| 6 | Pulse rise time delay (Tpt-Tsp) | $f(V_{FL})$ | None. Fixed or calibrated | time | None | Pulse delay vs. lamp voltage is characterized. Used to compensate Tpt, if needed. |
| 7 | Xe pulse | 10-30 | None. Fixed or calibrated | μs | None | |

Figure 10:
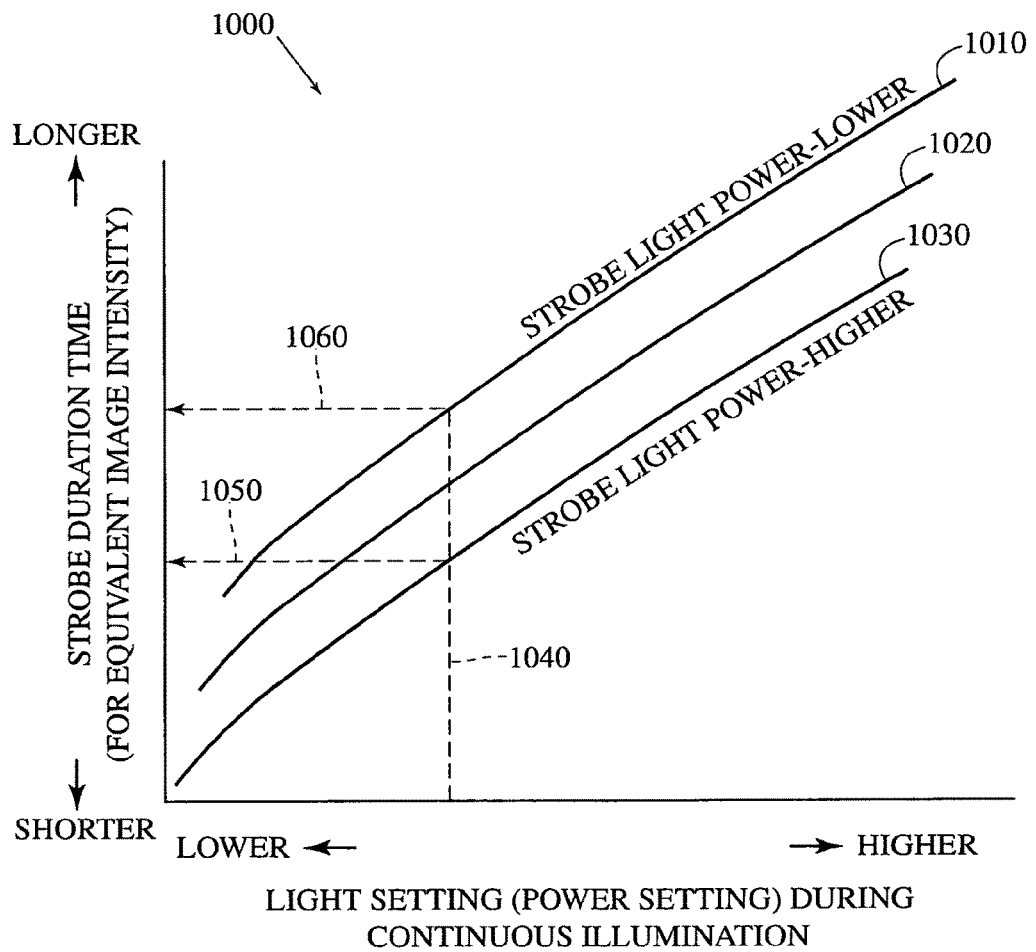
FIG. 10 shows a plot illustrating exemplary generic relationships between a power setting and corresponding strobe duration times.

FIG. 10 is a plot 1000 illustrating exemplary generic relationships between a light setting (power setting) during a continuous illumination that may be satisfactory during a reference or standard exposure time, and corresponding respective strobe duration times for a number of respective strobe light power levels represented by lines 1010, 1020, 1030. When using the light generation system 300 or 300' and the various systems and methods outlined above, particular strobe duration times may be implemented by controlling the various timing relationships outlined above with reference to FIGS. 7 and 8.

The abscissa in FIG. 10 may correspond to the light setting (power setting) during continuous illumination that produces a satisfactory "stationary" workpiece image that may be acquired throughout a reference or standard exposure time, such as the frame rate of conventional cameras. This method of illumination and exposure may be conventional, and may be well-suited for operation of a vision machine during manual operations and training mode operations that involve a machine operator. The ordinate in FIG. 10 may correspond to a strobe duration time necessary for a given strobe light power to achieve an image intensity equivalent to the light setting (power setting) during continuous illumination, that is, to achieve the same total exposure illumination energy for that light source.

A particular total exposure illumination energy may be defined as corresponding to a particular continuous illumination level, when using the reference or standard exposure time. This energy may be divided by a particular strobe light average power level that may directly determine the corresponding required strobe duration time to a first approximation. Each of the exemplary strobe light power curves 1010, 1020, 1030 may reflect a respective strobe lamp power setting consistent for each point along the respective curves. Thus, operation according to any point along the higher power curve 1030 may allow a shorter strobe duration time than operation according to corresponding (vertically aligned) points along either of the lower power curves 1020, 1010. When using the light generation system 300 or 300' and the various systems and methods outlined above, higher strobe light power curves may correspond to higher strobe lamp operating voltages and/or controlling the pixels of an LCD pixel array used for the SLM 350 to be fully transmitting. Lower strobe light power curves may correspond to lower strobe lamp operating voltages and/or controlling the pixels of an LCD pixel array used for the SLM 350 to be only partially transmitting.

In order to provide the shortest possible strobe duration and produce images having the least motion-related blur and the smallest possible uncertainty in the elevation distance, there are advantages to operating at a point toward the lower left end of any strobe light power curve.

Each strobe light source may inherently have a maximum allowable power level and, in the absence of other camera response considerations, and other analogous devices, this factor may determine the fastest allowed strobe duration. The higher power curve 1030 generally represents such a maximum power level. For a maximum or selected power level and a desired operating point, for example, as indicated by the line 1040, the corresponding strobe duration period may then be determined.

The strobe duration period may provide the required matching total exposure illumination energy. The lines 1050, 1060, generally represent alternative settings for providing a desired illumination level by using respective strobe duration times corresponding to respective strobe light power levels. Also, for a desired strobe duration time defined along the ordinate, the corresponding required strobe light power may be determined at the intersection of the abscissa and ordinate values in the plot 1000.

An operator may input control parameters such as workpiece positions, light source intensity mixtures, etc. to inspect one or more workpieces manually, semi-automatically, or automatically. An example of types of parameters that may be entered is shown in Table 3 below. Parameters such as workpiece image acquisition positions, stage velocity, magnification, light intensities, etc., may be provided.

TABLE 3

| | Parameter Name | Parameter Value |
|---|---|---|
| 1 | Workpiece Position(s) | X-, Y-, Z- coordinates |
| 2 | Stage Velocity | V |
| 3 | Ring light: % of available power or duty cycle | 100% |
| 4 | Coaxial light % of available power or duty cycle | 75% |
| 5 | Stage Light % of available power or duty cycle | 50% |
| 6 | Magnification | 1 x |
| 7 | Edge Position Tolerance or Allowable Blur | ±1.5 micron or ±0.25 pixels |
| 8 | etc. | etc. |

The parameters in Table 3 are only examples, and in particular situations, more, or fewer, or alternate parameters may be necessary for compatibility with different equipment designs.

The control parameters may be determined by an operator who places a sample workpiece 20 (FIG. 2) onto the stage 210 (FIG. 2) and determines the best position, magnification, lighting, etc., with which to perform the image capture to obtain optimal results. An operator may image a sample workpiece 20 with various parameter combinations and observe the image captured by the camera 260 (FIG. 2) and assess whether the edges are properly determined After obtaining an operable set of parameters, the operator may enter those parameter values as programmed control parameters.

The control system portion 120 may process the control parameters established by the operator that may be obtained during the static imaging conditions of a training mode and convert them to appropriate control commands for dynamic image capture during the continuous motion conditions of an automatic inspection mode. For example, successive image acquisition locations and the associated total illumination energy to be provided by each light source may be established by the operator during a training mode and the measurement path, velocities, SLM settings corresponding to the various light sources, effective strobe duration period corresponding to the various light sources, etc, may then be optimized by appropriate processing and/or analysis in the control system portion 120 (FIG. 2), in order to yield the highest throughput, or best accuracy, etc., during automatic inspection program execution. After the dynamic image capture control commands for the automatic inspection program have been generated, the control commands (and the control parameters) may be stored in the memory 140 for later retrieval and use.

After processing the control parameters and/or retrieving control commands from the memory 140 (FIG. 2), the control system portion 120 downloads image acquisition position parameters, the associated light control command information, and any other appropriate information to the lighting control interface 133 and/or the light channel exposure and control portion 135 and/or the light generation system 300 and may control the other system components to execute an inspection process. In various applications, it may be desirable to use the dedicated processing and deterministic timing of the light generation system 300 in order to simultaneously control the high speed light pulse patterns of multiple light sources with sufficient accuracy, and at the desired position along a high-speed motion path. For example, the motion controller 132 may receive stage velocity information and command the stage 210 to move the workpiece 20 after receiving position information from the light generation system 300, which may receive control commands from control system portion 120 and processes the control commands into specific data to control an image capture operation.

The captured images may be processed by the video tool portion 143. The image capture cycles may be repeated until completion of a total number of inspection images for each workpiece 20 (FIG. 1), and the control system portion 120 issues a next position signal corresponding to a next (if any) workpiece 20.

Figure 11:
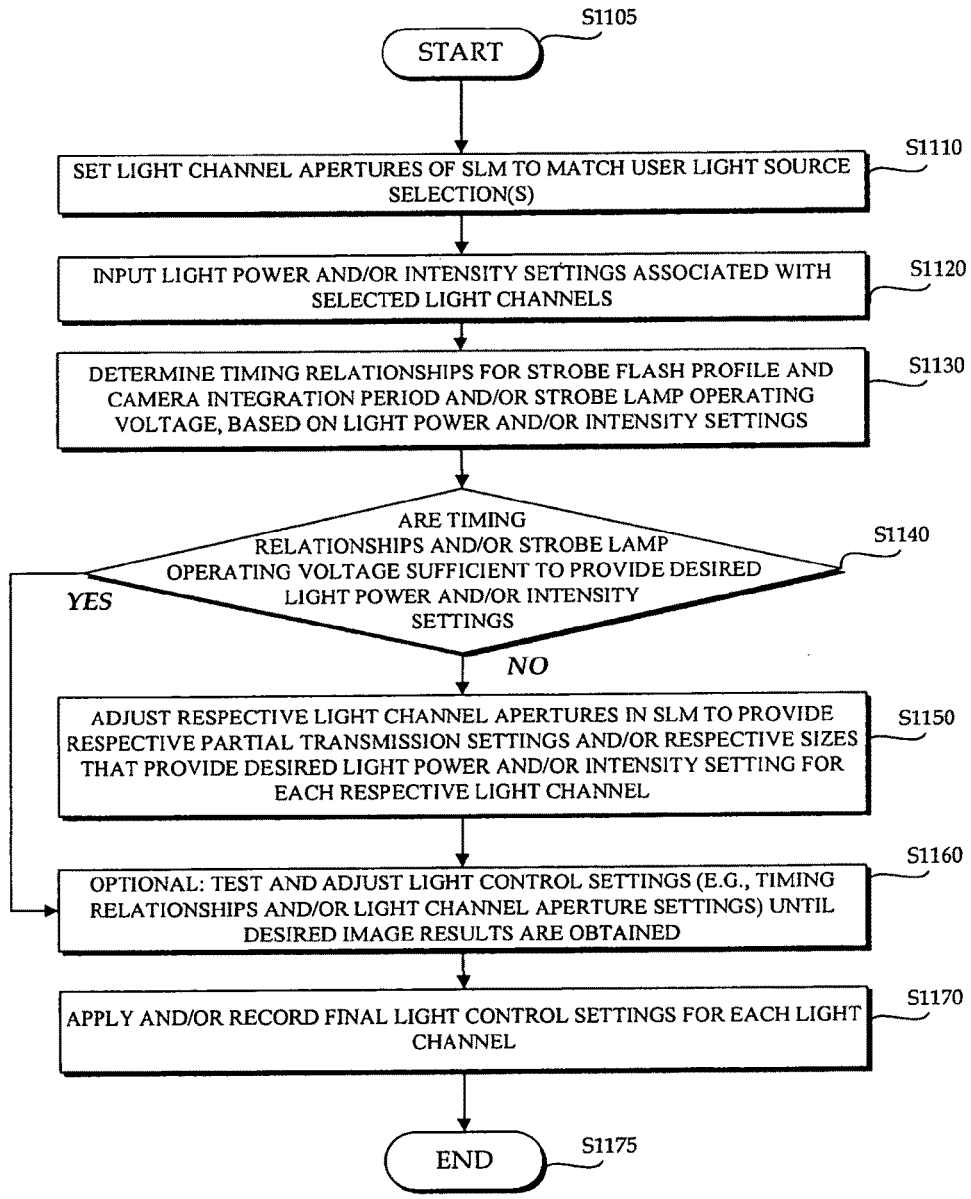
FIG. 11 is a flowchart illustrating an exemplary method of using a strobe light source and a spatial light modulator to provide illumination levels for one or more light sources.

FIG. 11 is a flowchart illustrating an exemplary method 1100 of using an a strobe light source and a spatial light modulator to provide desired illumination levels for one or more light sources in a machine vision inspection system. The operations shown in FIG. 11 may be executed, for example, during learn mode operations of the machine vision inspection system 10', in order to determine various light control parameters that may to be used to provide strobe illumination during run mode operations. The method may begin in step S1105 and proceed to step S1110, wherein the light channel apertures of a controllable SLM may be set to correspond to one of more light sources selected by a user to illuminate a workpiece feature to be inspected. For example, for light sources not selected by a user, the SLM may be controlled to set the corresponding light channel apertures to an "OFF" condition. The selected light channel apertures may be tentatively set to an "ON" condition. The method may then proceed to step S1120, wherein machine vision inspection system inputs the light power or intensity settings that are associated with the various selected light sources. The light power or intensity settings may be determined manually by a user, based on observation of real time images while the user adjusts the light sources during the learn mode operations, or automatically, based on methods taught in U.S. Pat. No. 6,627,863, which is incorporated herein by reference in its entirety. In some implementations, a light power setting of zero may indicate an "OFF" setting for a light source, and steps S1110 and S1120 may be merged or indistinguishable.

In step S1130, the machine vision inspection system may analyze the light power or intensity settings input in step S1120 and determine timing relationships between the strobe flash profile and the camera integration period, and/or a strobe lamp operating voltage, based on the light power or intensity settings, such that the strobe illumination that is integrated during the camera integration period provides an illumination level that is sufficient for all of the respective selected light source channels, in comparison to their respective light power or intensity settings. The control parameters corresponding to the determined timing and/or voltage level may be stored in memory and/or implemented in the appropriate circuits or routines. The corresponding strobe illumination level may exceed the respective light power or intensity settings for some or all of the light source channels, if a controllable SLM is available to attenuate the light transmission to the various light source channels. In a decision step S1140, it may be determined whether the timing and/or voltage level determined in step S1130 is sufficient to provide the desired light power and/or intensity setting for each selected light source. If so, then operation may jump to step S1160. Otherwise, operation proceeds to step S1150. In step S1150, the respective light channel apertures are adjusted in the SLM to provide respective partial light transmission settings and/or respective aperture sizes that provide a level of light transmission attenuation that provides the desired light power and/or intensity level for each respective light channel. It should be appreciated that a light channel aperture size can be reduced in the SLM, instead of, or in addition to adjusting the pixel graylevels or the like, in order to attenuate the light transmission through a light source channel aperture. It should be appreciated that in the step S1150, the SLM may be adjusted independently for each light source channel aperture, such that one strobe flash can be differently attenuated for each respective light source channel, to provide a desired combination of illumination levels for multiple light sources during a single flash.

In an optional step S1160, the light control settings determined in steps S1130-S1150 may be tested by acquiring and evaluating a workpiece image using the settings. For example, the user may observe the resulting image on a display of the machine vision inspection system during learn mode, and accept or reject the image. If the image is rejected, the light control settings may be refined and retested until an acceptable image results. However, if the image illumination is not critical for a particular image, and/or if the various light control settings are adequately accurate and/or calibrated such that reliable illumination levels are obtained without confirmation of the determined settings, then the step S1160 may be omitted. In step S1170 the final light control settings determined in steps S1130-S1160 may be applied to acquire a workpiece image suitable for learn mode inspection operations and/or recorded, for example, in a part program that may be used later for automatic high-speed inspection. The process may then end in step S1175.

Artisans having skill in the art will recognize and understand that various functions for the systems and methods for controlling strobe illumination may be performed in any manner among any quantity (e.g., one or many) of hardware and/or software modules or units, computers or processing systems or circuitry. The control system portions may be integrated within a stand-alone system or may be executed separately and be coupled to any number of devices, workstation computers, server computers or data storage devices via any communications medium (e.g., network, modem, direct connection, wireless transmission).

The control system processes may be implemented by any quantity of devices or processing systems (e.g., IBM-compatible, Apple, Palm Pilot, Blackberry). The computer system may include any commercially available or customized operating system (e.g., Windows, Macintosh, Unix, Linux, OS/2, DOS) to execute any commercially available or custom designed software (e.g., Quick Vision™) and any type of input devices (e.g., keyboard, mouse, microphone, I/O port, wireless receiver). It is to be understood that the software of the strobe illumination control may be implemented in any desired computer language (e.g., C, C++, Java, Fortran, Lisp, SQL), and could be developed by one of ordinary skill in the computer and/or programming arts based on the functional description contained herein. Moreover, such software may be available or distributed via any suitable medium (e.g., stored on magnetic or optical devices such as CD-ROM and diskette), downloaded from the internet or other network, downloaded from a bulletin board, or other conventional distribution mechanisms.

Figure 12:
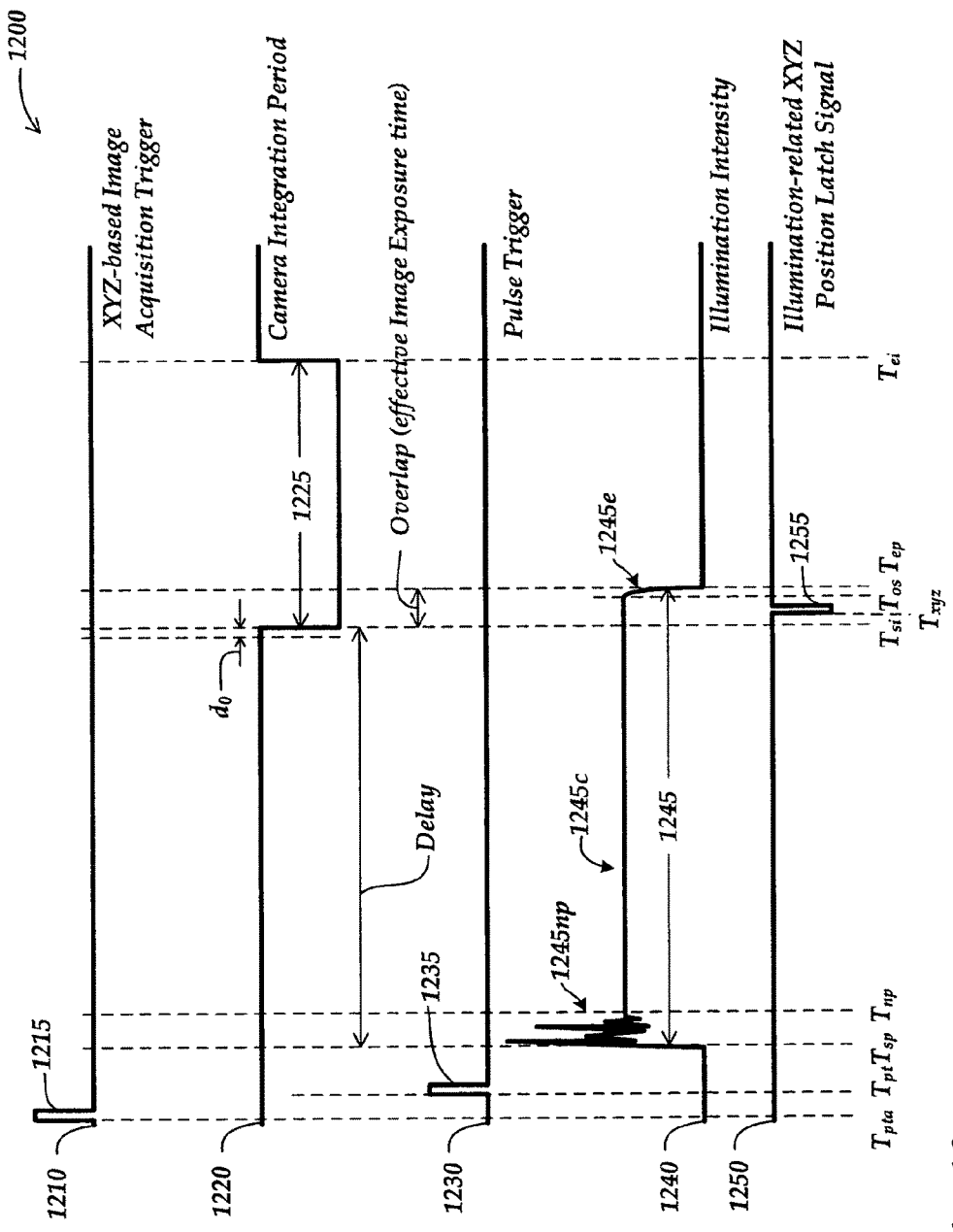
FIG. 12 shows an timeline chart corresponding to a second exemplary embodiment of signals for controlling a strobe pulse duration and a camera integration period associated with strobe illumination and exposure control.

FIG. 12 shows a timeline chart 1200 corresponding to a second exemplary embodiment of signals (e.g. trigger signals) for controlling a strobe pulse duration and a camera integration period associated with strobe illumination and exposure control. The timelines in the chart 1200 are analogous to the timelines in the chart 700 previously described with reference to FIG. 7, and analogous elements and times are numbered with similar suffixes (e.g. the numbers 710 and 1210 have the similar suffix "10") and/or similarly labeled, and may be understood by analogy with previous description. Therefore, only the significant differences in FIG. 12 are described in detail below.

As previously outlined, the timelines shown in FIG. 7 correspond to embodiments wherein the beginning of the exposure duration or camera integration period precedes the illumination pulse trigger and then ends during the illumination pulse, to allow for effective image exposure times which are less than both the illumination pulse duration and the camera integration period. Short image exposure times provided by this "overlap" control technique allow a clear "frozen" image of a workpiece at increased motion speeds, which increases inspection throughput. Such embodiments may be most suited to strobe illumination sources that use a high intensity Xenon (Xe) flashlamp, or the like, wherein the ability to precisely control the strobe pulse intensity profile (e.g. the decay rate of the strobe pulse) and/or duration is limited. Such embodiments may also be suited to systems and/or applications that use relatively longer strobe exposure times (e.g. on the order of microseconds).

In contrast, for strobe illumination sources that use high powered LEDs, wherein the pulse intensity profile and/or duration may be more precisely controlled, and/or where the shortest possible effective image exposure times are desired, embodiments corresponding to the timelines shown in FIG. 12, may be most suitable. Briefly, in such embodiments, the illumination pulse duration is triggered to start first, the camera integration period is triggered to start after a delay relative to the start of the illumination pulse duration, and the illumination pulse duration ends during the camera integration period, may be more advantageous for avoiding illumination noise and improving image exposure repeatability, while also providing shorter image exposure times, as outlined below.

In particular, increasingly powerful LED strobe sources allow and/or require shorter image exposure times. High power LED illumination which may include wavelength altering phosphor materials or the like and may have a drive current on the order of 40 A. For example, a single chip, monolithic PhlatLight LED from Luminus of Billerica, Mass. may be suitable as an LED strobe source. However, such strobe sources may include illumination noise components as described in greater below. It should be appreciated that decreasing exposure times means that any noise component (e.g. intensity variations) in the illumination pulse is averaged into a shorter image exposure time. As a result, image exposure repeatability suffers, particularly for shorter exposure times. Reduced image exposure repeatability degrades potential accuracy in certain operations (e.g. autofocus and/or focus height determination, as one example), introducing errors that are significant, particularly in precision machine vision inspection systems. Thus, it is important to further decrease and/or compensate illumination noise components that may otherwise be included in short image exposure times.

Powerful LED strobe sources may be driven using currents as large as 40 amperes (40 A), or more. An initial noise period of intensity noise of the illumination pulse may be associated with the transient circuit effects of starting such a high current pulse into the LED. Thus, in some embodiments, the control system portion is configured to control a timing relationship between the camera integration period and a pulse duration of the radiation emitted by the strobe light generator such that an image exposure of the camera image occurs during a timing overlap between a beginning of the camera integration period and an end of the pulse duration. In other words, the timing relationship is controlled such that the illumination pulse duration starts, the camera integration period begins after a delay relative to a start of the pulse duration and not later than the end of the pulse duration, and the pulse duration may end before the camera integration period ends. By providing the image exposure during the timing overlap at the end of the pulse duration, the aforementioned initial noise period of the illumination pulse duration is avoided, in order to provide more repeatable image illumination levels (e.g. for repeated images, such as an image stack that is acquired and used in various known autofocus operations). Thus, this method provides the ability to increase the dynamic range of exposures for which simple time-based control may be used, without degrading repeatability of the exposure level, even for very short pulse durations.

The chart 1200 includes five timelines analogous to those shown in FIG. 7. A timeline 1210 represents an image acquisition trigger signal 1215 beginning at a position trigger time $T_{pta}$ based on positional X-, Y- and Z-axis coordinates of the stage 210 (see FIG. 2). A timeline 1220 represents a camera integration period 1225, having a programmable duration starting at time $T_{si}$ and ending at $T_{ei}$, controlled based on a high-speed clock, such that it is relatively consistent (although various cameras may require a minimum integration period that spans several clock cycles). The timeline 1230 represents the flash initiation signal 1235, beginning at a pulse trigger time $T_{pt}$ initiated based on the position trigger time $T_{pta}$ (e.g. based on a fixed circuit latency or a programmed delay) to trigger the strobe flash or pulse indicated by the timeline 1240. The start time $T_{sp}$ of the pulse duration may occur with a discrete latency period ($T_{sp}$-$T_{pt}$) after the pulse trigger time $T_{pt}$ has been used to trigger the strobe pulse. However, the latency period may be relatively consistent. In various implementations, the pulse trigger time $T_{pt}$ may be based on, or may start, the same high-speed clock that is used to determine the camera integration duration 1225. Therefore, in such embodiments the effective delay of the start time $T_{si}$ of the camera integration period may be programmable to be consistent relative to the start time $T_{sp}$ of the strobe pulse duration 1245, based on the high-speed clock. The pulse duration 1245 may be constant based on known circuit design techniques, in some embodiments, or may be precisely programmed based on the high speed clock in other embodiments. Therefore, the overlap between the start time $T_{si}$ of the camera integration period and the end time $T_{ep}$ of the pulse duration may be precisely controlled, in order to determine the image exposure. The image exposure may be stopped by ending the pulse duration, and the camera integration period may be ended at a desired time thereafter.

As outlined previously, the illumination intensity immediately after the start of the pulse duration 1245 may be unstable or noisy during a noisy pulse portion 1245np, between the time $T_{sp}$ and a time $T_{np}$, due to transient circuit effects associated with starting a high current through the illumination source. However, the pulse intensity may be stable or consistent during a pulse portion 1245c, until an ending portion 1245e of the pulse duration 1245. Therefore, it is advantageous to begin the image integration period after a delay relative to a start of the pulse duration (e.g. a delay such that $T_{si}$ follows $T_{np}$), in order to start the image exposure during the stable portion 1245c of the pulse duration 1245, and avoid the intensity noise. In some embodiments, it is desirable for the pulse duration to be set at a value in a range of 50-150 μs (or even as low as 5 μs with extremely bright strobe illumination), for example, and to provide a delay of at least 15 μs in order for intensity instabilities to settle. In other embodiments, a delay of at least 25 μs may be more desirable. Of course, the delay must start the camera integration period to be no later than the end of the pulse duration 1245, otherwise the strobe pulse cannot illuminate the image.

The timeline 1250 represents an exposure-related coordinate position latch signal 1255 beginning at latch time $T_{xyz}$ that may coincide with an effective or nominal exposure time according to previously outlined principles. The X-, Y- and Z-coordinates for the stage 210 or the workpiece 20 at the latch time $T_{xyz}$ may be associated with the acquired image and may be stored in memory 140, as previously described.

The timing relationships shown in FIG. 12 and described above may be controlled to provide a desired overlap time $(T_{ep}\text{-}T_{si})$ and thereby control the corresponding effective image illumination over a wide dynamic range. In some embodiments, the machine vision system comprises an image brightness control and the control system portion is configured to control the overlap time $(T_{ep}\text{-}T_{si})$ based on a setting of the image brightness control. For example, this may be governed by a user interface wherein a user may adjust a level of image exposure with the image brightness control. In one embodiment, the control system portion may be configured to set the pulse duration $(T_{ep}\text{-}T_{sp})$ to a constant value and control the delay $(T_{si}\text{-}T_{sp})$ based on the setting of the image brightness control, such that the overlap time $(T_{ep}\text{-}T_{si})$ is "indirectly" controlled. In another embodiment, the control system portion is configured to set the delay $(T_{si}\text{-}T_{sp})$ to a constant value and control the pulse duration $(T_{ep}\text{-}T_{sp})$ based on the setting of the image brightness control, i.e. such that the overlap time $(T_{ep}\text{-}T_{si})$ is "indirectly" controlled. In another embodiment, the control system portion is configured to determine the time $T_{si}$ (e.g. by precisely triggering or detecting the start of the camera integration period at the time $T_{si}$ and triggering the end of the pulse duration $T_{ep}$ at a particular overlap delay governed by a high speed clock such that the overlap time $(T_{ep}\text{-}T_{si})$ is directly controlled based on controlling the overlap delay according to the setting of the image brightness control. In summary, in some embodiments, the control system comprises a high speed clock, and the setting of the image brightness control corresponds to a range of adjustment time units that adjust the timing of $T_{si}$, or $T_{ep}$, or both, directly or indirectly, as outlined above. In one example embodiment, the range of adjustment time units may comprise 100 units, corresponding to an overlap time range of 0 to 50 µs, with each adjustment time unit corresponding to an increment of 0.5 µs. A maximum light control setting of 100 units therefore corresponds to a maximum image exposure overlap time of 50 µs. However, this example is not limiting. In various embodiments, the resolution of brightness control is limited only by the clock speed that is used to control the overlap period $(T_{ep}\text{-}T_{si})$ that governs the image exposure. For example, a clock speed of 25 MHz may provide adjustment time units as fine as 40 ns.

In some embodiments, the image brightness control comprises a lowest setting which corresponds to a state wherein the overlap time $(T_{ep}\text{-}T_{si})$ is set to approximately zero, which may cause the lowest setting to operate such that pixel signals output by the camera as a result of an image exposure of a bright object at that setting are at or just above their lowest level (e.g. at a minimum limit value of zero, one or two for an 8-bit grey level signal). Such a setting is useful for imaging highly reflective workpieces, for example. In some embodiments, in order to accomplish this calibration of the brightness controls of the machine vision inspection system, the control system comprises an overlap calibration portion configured to define a timing offset $d_0$ that provides a desired pixel signal level (e.g. a minimum limit signal level) for a particular low level brightness setting (e.g. the minimum brightness setting). The timing offset $d_0$ is a fixed timing offset that the control system consistently adds to (or subtracts from) one or more timings that determine the overlap time (e.g. the timing of $T_{si}$, or $T_{ep}$, or both, directly or indirectly) in order to compensate for various component tolerances, various circuit timing latencies, and the like. The timing offset $d_0$ may be selected such that when the image brightness control comprises a lowest setting, it corresponds to a state wherein the overlap time $(T_{ep}\text{-}T_{si})$ is set to approximately zero, as outlined above. In some embodiments that use a high speed clock (e.g. 25 MHz, or more) to provide adjustment time units that govern the effective exposure time, the overlap time may be considered to be set to approximately zero when $(T_{ep}\text{-}T_{si})$ is at most 5 clock cycles, or less. It should be appreciated that a system using the timing relationships and adjustment principles described herein with respect to FIG. 12 allows for a large overlap time at a lower cost than a system using other timing or illumination arrangements (e.g. the timing relationships in FIG. 7), while allowing for very fine image brightness control and ease of use.

Figure 13B:
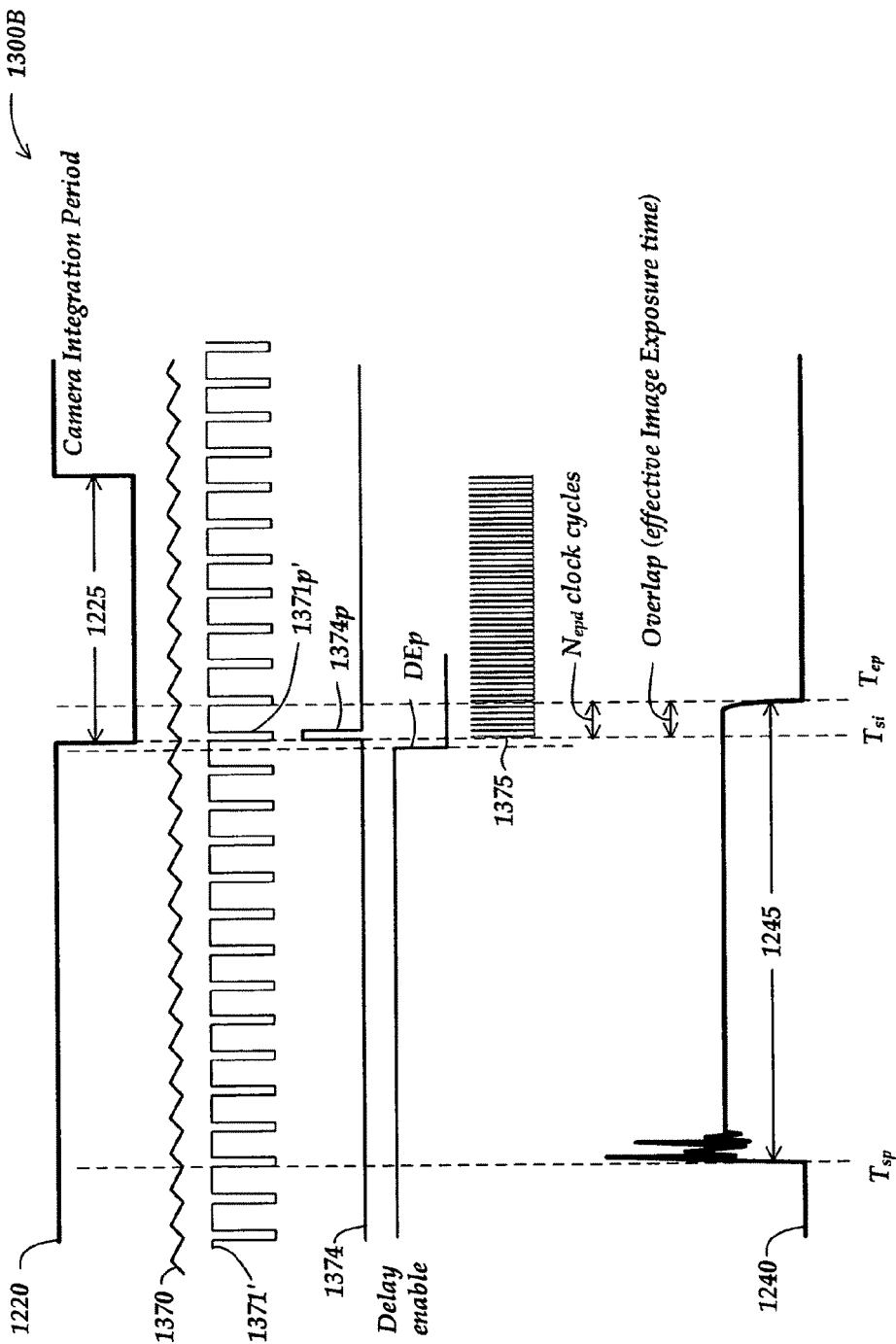

FIGS. 13A and 13B show timing diagrams illustrative of first and second techniques, respectively, usable for synchronizing an image exposure with a periodic ripple component in illumination intensity in a third embodiment of exemplary camera and flash triggers associated with strobe illumination and exposure control. A periodic ripple component in the illumination intensity, which may arise due to a corresponding ripple in the high-current drive circuit, is a potential source of non-repeatable illumination levels from powerful LED strobe sources. It is difficult to economically eliminate such ripple components (e.g. on the order of 1-2% of the drive level) in high current drive circuits that must provide fast on/off switching times for strobe control. It should be appreciated that if different image exposures have the same effective exposure length (e.g. the same "overlap" time outlined above), but are timed differently relative to the phase of the periodic ripple, then both the instantaneous and average illumination intensity may vary despite the otherwise consistent effective exposure length. This may affect the accuracy and/or repeatability of images used for edge detection, autofocus, and the like, at a level that is significant for precision machine vision inspection systems. Therefore, in some embodiments, the control system portion is configured to synchronize the signals that control the image exposure timing with the periodic ripple component. This further improves the repeatability of image illumination levels, especially for very short pulse durations.

FIG. 13A shows a timing diagram 1300A corresponding to a first technique for consistently synchronizing the image exposure (e.g. the overlap time) with the ripple component outlined above. The chart 1300 includes a timeline 1210 that represents an image acquisition trigger signal 1215 beginning at a position trigger time $T_{pta}$ based on positional X-, Y- and Z-axis coordinates as previously outlined (e.g. with reference to FIG. 7). A timeline 1370 represents the ripple component in the drive signal and/or illumination intensity, outlined above (a large DC component of the drive signal and/or illumination intensity is not shown). A timeline 1371 represents a periodic digital signal including pulses 1371p derived from the ripple component 1370 by known techniques (e.g. by known comparator circuits, or the like.) A timeline 1372 represents a synchronization pulse 1372p derived from the image acquisition trigger signal 1215 and a pulses 1371p derived from the ripple component 1370. In one embodiment, the synchronization pulse 1372p is created by inputting the signals of the timelines 1210 and 1371 into an AND circuit of a known configuration, and the synchronization pulse 1372p arises at the output of the AND circuit. It will be appreciated that in various embodiments, the period and duration of the pulses 1371p may be known by design or experiment, and the acquisition trigger signal 1215 may be designed to have a duration that is certain to overlap with the leading edge of one of the pulses, in order to generate the synchronization pulse 1372p.

A timeline 1373 represents counted pulses of a high speed clock signal, wherein the clock signal or the counting is started based on the synchronization pulse 1372p. The timeline 1230 represents the flash initiation signal 1235, beginning at a pulse trigger time $T_{pt}$, which may be used in the manner previously described with reference to FIG. 12, to trigger the start of the pulse duration 1245 as shown in the timeline 1240 of FIG. 12. In this embodiment, as shown in FIG. 13A, the flash initiation signal 1235, beginning at a pulse trigger time $T_{pt}$, is initiated at a desired number of clock cycles Npt represented on the timeline 1373. Thus, according to the sequence outlined above, the pulse trigger time $T_{pt}$ and the resulting illumination pulse duration 1245 (shown in FIG. 12) may be consistently synchronized with the ripple component represented in the timeline 1370, within approximately one cycle of the high speed clock (e.g. 40 nS), or less. As previously outlined with reference to FIG. 12, the timing of the camera integration period, and thus the overlap time $(T_{ep}\text{-}T_{si})$ may also be controlled based on the high speed clock (e.g. as represented in the timeline 1373), and therefore may be similarly consistently synchronized with the ripple component represented in the timeline 1370. Thus, the image exposure during the overlap time $(T_{ep}\text{-}T_{si})$ (shown in FIG. 12) may be repeatable for a given exposure control setting, despite the ripple component outlined above. It will be appreciated that in some embodiments, the ripple component may cause a control input/output curve to exhibit small local non-linearities, but the output associated with each control input will be repeatable according to the principles outlined above. In other embodiments, the repeatability may allow a calibration procedure to be used to precisely linearize the input/output curve, if desired. The ripple component may have a period on the order of 7 microseconds, in various embodiments, whereas the high speed clock may allow timing control increments on the order of 40 nS. Therefore, various timings may be adjusted in small increments relative to the ripple component, such that its effects may be compensated in brightness control settings, if desired.

FIG. 13B shows a timing diagram 1300B corresponding to a second technique for consistently synchronizing the image exposure overlap time with the ripple component outlined above. Reference numbers that are similar in FIG. 13B, 13A and FIG. 12 describe analogous or identical elements. The chart 1300B assumes that the signals shown in timelines of FIG. 12 may be generated approximately according to the previous description of FIG. 12, except for the specific details disclosed below. In particular, the timeline 1240 represents the pulse duration 1245, which may be initiated as previously outlined with reference to FIG. 12, and the timeline 1220 represents the camera integration period 1225. A delay enable timeline not shown in previous figures shows a delay enable pulse DEp which may be programmed to occur at a nominal delay time relative to the pulse duration start time $T_{sp}$, or a related signal (e.g. as determined by a system clock). The timeline 1370 represents the ripple component in the drive signal and/or illumination intensity, as outlined previously with reference to FIG. 13A. The timeline 1371' represents a periodic digital signal including pulses 1371p' derived from the ripple component 1370 by known techniques (e.g. by known comparator circuits, or the like.) A timeline 1374 represents a synchronization pulse 1374p derived from the delay enable pulse DEp and a pulse 1371p' derived from the ripple component 1370. In one embodiment, the synchronization pulse 1374p is created by inputting the signal of the timeline 1371' and the delay enable signal DEp into an AND circuit of a known configuration that is enabled for a single output pulse, and the synchronization pulse 1374p arises at the output of the AND circuit. It will be appreciated that the synchronization pulse 1374p may start within approximately one period of the ripple component (e.g. on the order of 7 microseconds, in one embodiment) relative to the timing of the delay enable pulse DEp.

The synchronization pulse 1374p starts the camera integration period 1225 at the time Tsi, and initiates the counted pulses of a high speed clock signal as represented in the timeline 1375. In this embodiment, as shown in FIG. 13B, the pulse duration 1245 is ended at the time $T_{ep}$ based on a desired number of clock cycles Nepd after the camera integration period start. Thus, according to the sequence outlined above, the overlap time $(T_{ep}\text{-}T_{si})$ may be consistently synchronized with the ripple component represented in the timeline 1370, and precisely controlled based on the high speed clock. Thus, the image exposure during the overlap time $(T_{ep}\text{-}T_{si})$ may be repeatable for a given exposure control setting, despite the ripple component.

Figure 14B:
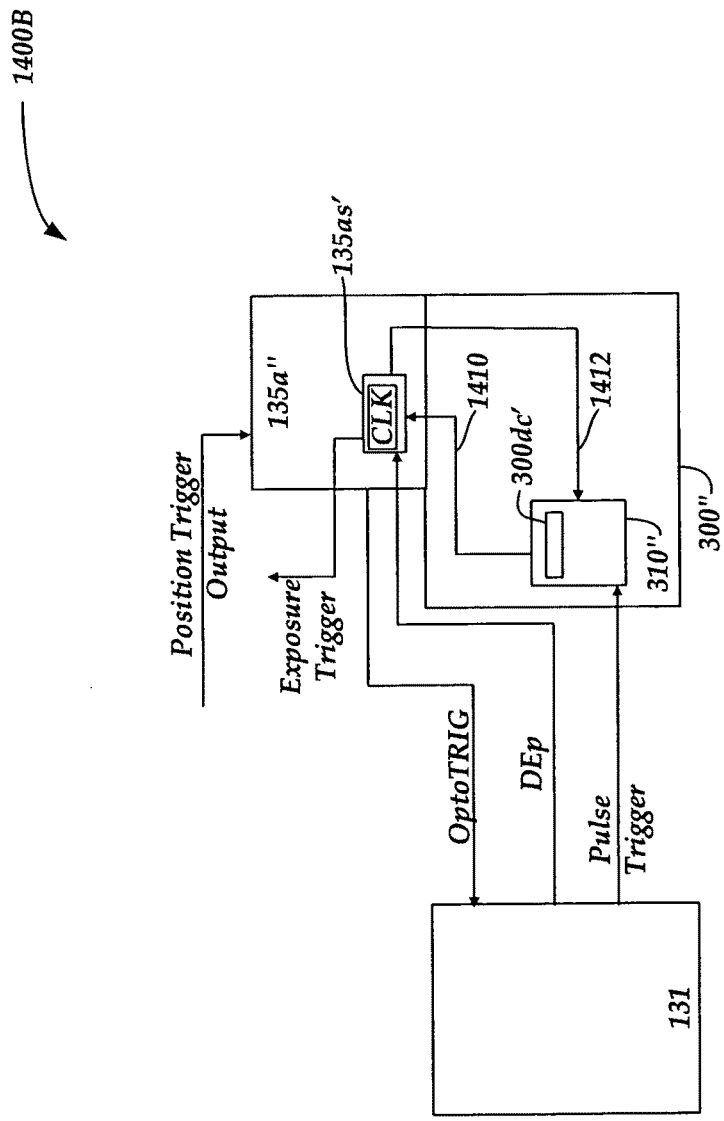

FIGS. 14A and 14B show block diagrams of exemplary controller circuits and signals associated with a light generator and a vision measuring machine, usable to generate the signals shown in FIGS. 13A and 13B, respectively. FIGS. 14A and 14B show a block diagrams 1400A and 1400B, respectively, of alternative embodiments of components previously shown and described with reference to FIG. 8. Similar reference numbers in FIG. 14A, 14B, and FIG. 8 (e.g. the reference numbers 310 and 310' are similar) refer to analogous elements, and the components of FIGS. 14A and/or 14B may be understood to operate within a larger system, approximately as outlined with reference to FIG. 8.

The components of FIG. 14A, may used to implement the signals of FIG. 13A. In this embodiment, a strobe light generator 310' of the light generator system 300' may include a high power LED illumination source and a drive circuit that provides a drive signal that provides power to the illumination source. The drive signal may exhibit a periodic ripple component, as outlined above. The light generator system 300' may include a ripple detection circuit portion 300dc, which is configured to be connected to the drive circuit of the light generator 310', and to input and/or sense the ripple component 1370 and output the pulses 1371p previously shown and described with reference to FIG. 13A, according to known signal processing techniques. In the embodiment shown in FIG. 14A, the pulses 1371p are output on the signal line(s) 1310 to a synchronization circuit 135as included in the timing and synchronization portion 135a'. The synchronization circuit 135as may also receive a position trigger output signal (see 1215, FIG. 12) from the motion control interface 132 (see FIG. 8), and send the timing signal "OptoTRIG" to the imaging control interface 131. The signal OptoTRIG may correspond to, or be identical to, the signal pulse 1372 shown in FIG. 13A. The imaging control interface 131 may include a high speed clock that generates and/or counts the clock pulses shown in the timeline 1373 of FIG. 13A and generates the signal "Pulse Trigger", which may correspond to, or be identical to, the signal pulse 1235 shown in FIG. 13A. That signal may trigger the strobe light generator 310' to start the pulse duration 1245 as previously outlined with reference to FIG. 13A and FIG. 12. The imaging control interface 131 may also generate the other timing relationships previously described with reference to FIG. 13A and FIG. 12.

The components of FIG. 14B, may be used to implement the signals of FIG. 13B. In this embodiment, a strobe light generator 310" of the light generator system 300" may include a high power LED illumination source and a drive circuit that provides a drive signal that provides power to the illumination source. The drive signal may exhibit a periodic ripple component, as outlined above. The light generator system 300" may include a ripple detection circuit portion 300dc', which is configured to be connected to the drive circuit of the light generator 310", and to input and/or sense the ripple component 1370 and output the pulses 1371p' previously shown and described with reference to FIG. 13B, according to known signal processing techniques. In the embodiment shown in FIG. 14B, the pulses 1371p' are output on the signal line(s) 1410 to a synchronization circuit 135as' included in the timing and synchronization portion 135a".

The timing and synchronization portion 135a" may receive a position trigger output signal (see 1215, FIG. 12) from the motion control interface 132 (see FIG. 8), and send the timing signal "OptoTRIG" to the imaging control interface 131. The imaging control interface 131 may include a high speed clock, and at an appropriated time may generate the signal "Pulse Trigger" which may trigger the strobe light generator 310" to start the pulse duration 1245 as previously outlined with reference to FIG. 13B and FIG. 12. The imaging control interface 131 may also generate and output the delay enable pulse DEp shown and described with reference to FIG. 13B. The synchronization circuit 135as' may input the delay enable pulse DEp, and the pulses 1371p' from the ripple detection circuit 300dc', and generate the Exposure Trigger signal (e.g. using a known AND circuit that outputs a single pulse, which may be identical to the synchronization signal 1374p, shown and described with reference to FIG. 13B. In this embodiment, the synchronization circuit 135as' outputs the Exposure Trigger to start the camera integration period. It also includes a high speed clock that generates and/or counts the clock pulses shown in the timeline 1375 of FIG. 13B and generates a signal that is output on the signal line(s) 1412 to trigger the strobe light generator 310" to end the pulse duration 1245 as previously outlined with reference to FIG. 13B and FIG. 12.

It should be appreciated that the foregoing principles regarding synchronizing an effective image exposure time with a ripple component in a strobe illumination intensity may be used more generally to advantage, regardless of the details of how the image exposure time is controlled. For example, more generally, the ripple component synchronization principles outlined above may be used when the start and end of an effective image exposure time are determined as outlined above, or determined solely by the start and end of a pulse duration that is embedded within a camera integration period, or determined solely by the start and end of a camera integration period that is embedded within a pulse duration, or determined by the start of a pulse duration and the end of an overlapping camera integration period (e.g. as shown in FIG. 7). In each case, synchronizing an effective image exposure time with a ripple component in a strobe illumination intensity will improve the repeatability of the associated image exposure.

Figure 15:
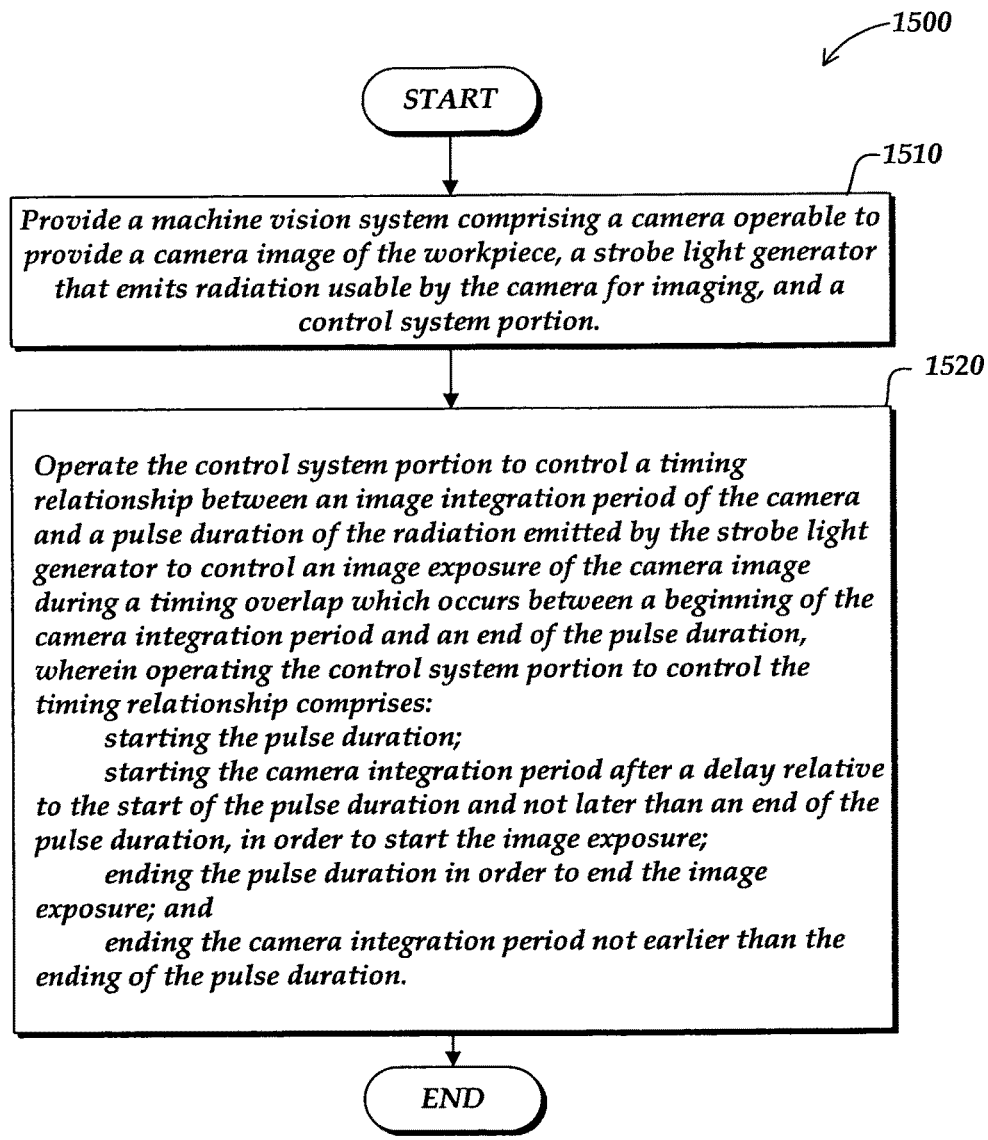
FIG. 15 is a flowchart illustrating one exemplary method of providing strobe illumination and exposure control corresponding to principles illustrated by the timing diagrams of FIGS. 12, 13A, and 13B.

FIG. 15 shows a flowchart 1500 illustrating one exemplary method of providing strobe illumination and exposure control corresponding to principles described above with reference to FIGS. 12, and/or 13A or 13B. The method starts and at a block 1510, a machine vision system is provided comprising a camera operable to provide a camera image of a workpiece, a strobe light generator that emits radiation usable by the camera for imaging, and a control system portion.

Next, at a block 1520, the control system portion is operated to control a timing relationship between an image integration period of the camera and a pulse duration of the radiation emitted by the strobe light generator, to control an image exposure of the camera image during a timing overlap which occurs between a beginning of the camera integration period and an end of the pulse duration, wherein operating the control system portion to control the timing relationship comprises: starting the pulse duration; starting the camera integration period after a delay relative to a start of the pulse duration and not later than the end of the pulse duration, in order to start the image exposure; ending the pulse duration in order to stop the image exposure; ending the camera integration period not earlier than the ending of the pulse duration. In various embodiments, the camera integration period may end after the ending of the pulse duration. After the operations of block 1520 the method may end. In various embodiments, the operations of the block 1520 may be implemented as outlined above with reference to FIGS. 12-14. However, such embodiments are exemplary only, and not limiting. One of ordinary skill in the art may recognize alternative implementations, based on the principles and teachings disclosed herein.

It will be appreciated that various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art, and are also intended to be encompassed by the following claims.

What is claimed is:

1. A machine vision system that controls image exposure strobe illumination used to illuminate a workpiece, such that the workpiece may be imaged by a camera in the machine vision system while moving at high speed, the system comprising:
   a camera providing a camera image of the workpiece;
   a strobe light generator that emits radiation used by the camera for imaging; and
   a controller configured to control a timing relationship between an image integration period of the camera and a pulse duration of the radiation emitted by the strobe light generator to control an image exposure of a camera image during a timing overlap which occurs between a beginning of the image integration period and an end of the pulse duration, wherein the timing relationship is controlled such that the pulse duration starts, the image integration begins after a delay relative to a start of the pulse duration and not later than the end of the pulse duration, the pulse duration ends, and the image integration period ends not earlier that the end of the pulse duration.

2. The machine vision system of claim 1, wherein the timing relationship is further controlled such that the image integration period ends after the end of the pulse duration.

3. The machine vision system of claim 1, wherein the controller is further configured to control the delay to be at least 25 μs.

4. The machine vision system of claim 1, wherein the controller is further configured to variably control a length of the timing overlap in order to variably control the image exposure of the camera image.

5. The machine vision system of claim 4, wherein the controller is further configured to set the pulse duration to a constant value and to control the delay in order to control the length of the timing overlap.

6. The machine vision system of claim 5, wherein the controller is further configured to control the pulse duration to be in a range of least 5 μs and at most 150 μs.

7. The machine vision system of claim 4, wherein the controller is further configured to set the delay to a constant value and to control the pulse duration in order to control the length of the timing overlap.

8. The machine vision system of claim 4,
wherein the controller is further configured to control the length of the timing overlap based on an image brightness control setting.

9. The machine vision system of claim 8, wherein the image brightness control setting includes a lowest setting which corresponds to a state in which the length of the timing overlap is approximately zero.

10. The machine vision system of claim 9, wherein the controller is configured (1) to define a timing offset $d_0$ that is a fixed timing offset that the controller consistently adds to or subtracts from one or more timings that determine the length of the timing overlap, and (2) to make the timing offset $d_0$ cause the length of the timing overlap to be approximately zero when the image brightness control setting is at the lowest setting.

11. The machine vision system of claim 8, further comprises a clock used to control the timing relationship, and the image brightness control setting includes a lowest setting which corresponds to a state in which the length of the timing overlap is at most 5 clock cycles.

12. The machine vision system of claim 8, further comprises a clock used to control the timing relationship, and a range of settings of the image brightness control setting corresponds to a range of settings for a number of clock cycles that define the length of the timing overlap.

13. The machine vision system of claim 1, wherein
the strobe light generator comprises an illumination source and a drive circuit, the drive circuit providing a drive signal to power the illumination source, the drive signal exhibiting a periodic ripple component, and
the controller is further configured to consistently synchronize the end of the timing overlap relative to the periodic ripple component.

14. The machine vision system of claim 13, wherein the controller is configured to set the pulse duration to a constant value, and to consistently synchronize the start of the pulse duration relative to the periodic ripple component, and control the delay in order to control the length of the timing overlap.

15. The machine vision system of claim 1, wherein
the strobe light generator comprises an illumination source and a drive circuit, the drive circuit providing a drive signal to power the illumination source, the drive signal exhibiting a periodic ripple component, and
the controller is further configured to consistently synchronize the start of the timing overlap relative to the periodic ripple component.

16. The machine vision system of claim 15, further comprises a clock, wherein the controller is further configured to consistently synchronize the beginning of the image integration period relative to the periodic ripple component and the end of the pulse duration based on a number of clock cycles relative to the beginning of the image integration period, in order to control the length of the timing overlap.

17. The machine vision system of claim 1, further comprising a controllable spatial light modulator configured to provide a light channel aperture positioned to controllably attenuate the radiation emitted by the strobe light generator,
wherein the controller is further configured to control the image exposure of the camera image based on controlling the timing overlap which occurs between a beginning of the image integration period and an end of the pulse duration, in combination with controlling the light channel aperture to attenuate the radiation emitted by the strobe light generator.

18. A machine vision system that controls image exposure strobe illumination used to illuminate a workpiece, such that the workpiece may be imaged by a camera in the machine vision system while moving at high speed, the system comprising:
a camera that provides a camera image of the workpiece;
a strobe light generator that emits radiation used by the camera for imaging; and
a controller configured to control a timing relationship between an image integration period of the camera and a pulse duration of the radiation emitted by the strobe light generator to control an image exposure of the camera image during a timing overlap which occurs between the image integration period and the pulse duration,
wherein the machine vision system is configured according
the timing relationship being controlled such that the pulse duration starts, the camera integration begins after a delay relative to the start of the pulse duration and not later than an end of the pulse duration, the pulse duration ends, and the image integration period ends after the end of the pulse duration, and
the strobe light generator comprises an illumination source and a drive circuit, the drive circuit providing a drive signal to power the illumination source, the drive signal exhibiting a periodic ripple component, and the controller being configured to consistently synchronize one of the start and the end of the timing overlap relative to the periodic ripple component.

19. A method for controlling image exposure strobe illumination used to illuminate a workpiece in a machine vision inspection system, such that the workpiece may be imaged by a camera in the machine vision system while moving at high speed, the method comprising:
providing a machine vision system comprising a camera that provides a camera image of the workpiece, a strobe light generator that emits radiation used by the camera for imaging, and a controller; and
operating the controller to control a timing relationship between an image integration period of the camera and a pulse duration of the radiation emitted by the strobe light generator to control an image exposure of the camera image during a timing overlap which occurs between a beginning of the image integration period and an end of the pulse duration, wherein the operating the controller to control the timing relationship comprises:
starting the pulse duration;
beginning the image integration period after a delay relative to a start of the pulse duration and not later than the end of the pulse duration, in order to start the image exposure;
ending the pulse duration in order to stop the image exposure; and ending the image integration period not earlier than the ending of the pulse duration.

* * * * *